United States Patent
Yao et al.

(10) Patent No.: US 10,729,901 B2
(45) Date of Patent: Aug. 4, 2020

(54) IMPLANTABLE ELECTRODES COMPRISING MECHANICALLY CONSTRAINED BIOCOMPATIBLE HYDROGELS WITH CONDUCTIVE PASSTHROUGH

(71) Applicant: Verily Life Sciences LLC, South San Francisco, CA (US)

(72) Inventors: Huanfen Yao, Brisbane, CA (US); Kimberly Kam, Orinda, CA (US); Daniel Otts, Pleasanton, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 263 days.

(21) Appl. No.: 15/811,774

(22) Filed: Nov. 14, 2017

(65) Prior Publication Data
US 2018/0133457 A1 May 17, 2018

Related U.S. Application Data

(60) Provisional application No. 62/421,702, filed on Nov. 14, 2016.

(51) Int. Cl.
*A61N 1/05* (2006.01)
*A61B 5/04* (2006.01)
*A61B 5/00* (2006.01)

(52) U.S. Cl.
CPC .......... *A61N 1/05* (2013.01); *A61B 5/04* (2013.01); *A61B 5/686* (2013.01); *A61B 5/6867* (2013.01);
(Continued)

(58) Field of Classification Search
CPC ........ A61N 1/05; A61B 5/686; A61B 5/6846; A61B 5/6867; A61B 2562/0209;
(Continued)

(56) References Cited

U.S. PATENT DOCUMENTS

| 5,511,548 A | 4/1996 | Riazzi et al. |
| 5,931,862 A * | 8/1999 | Carson ................. A61N 1/0563 607/116 |

(Continued)

FOREIGN PATENT DOCUMENTS

| AU | 2014268188 | 12/2014 |
| WO | 0019892 | 4/2000 |

(Continued)

OTHER PUBLICATIONS

Aregueta-Robles et al., "Organic Electrode Coatings for next-Generation Neural Interfaces", Frontiers in Neuroengineering 7 (2014): 15.

(Continued)

*Primary Examiner* — Linda C Dvorak
*Assistant Examiner* — James A Cipriano
(74) *Attorney, Agent, or Firm* — Kilpatrick Townsend & Stockton LLP

(57) ABSTRACT

Biomaterials, such as hydrogels, can be mechanically secured to an electrode of an implantable device using a non-swellable shell. Hydrogel can be applied to an electrode surface and then mechanically constrained in place by a non-swellable shell. The non-swellable material can be secured to a substrate supporting an electrode or can otherwise surround an electrode and the hydrogel. The non-swellable shell can include openings or passthroughs that allow for electrical conduction across the non-swellable shell. The hydrogel can extend out of the openings to contact adjacent biological tissue. In some cases, an outer layer of hydrogel can surround the non-swellable shell and connected to the inner layer of hydrogel through the openings of the non-swellable shell.

29 Claims, 16 Drawing Sheets

(52) U.S. Cl.
  CPC .......... *A61B 2562/0209* (2013.01); *A61B 2562/0217* (2017.08); *A61B 2562/046* (2013.01); *A61B 2562/125* (2013.01); *A61B 2562/14* (2013.01)

(58) Field of Classification Search
  CPC ........ A61B 2562/046; A61B 2562/125; A61B 2562/14; A61B 2562/0217
  See application file for complete search history.

(56) References Cited

U.S. PATENT DOCUMENTS

| | | |
|---|---|---|
| 2011/0087315 A1 | 4/2011 | Richardson-Burns et al. |
| 2013/0030353 A1* | 1/2013 | Seymour .............. A61N 5/0622 604/20 |
| 2015/0073520 A1 | 3/2015 | Strahl et al. |
| 2016/0213913 A1* | 7/2016 | Dhanasingh ......... A61N 1/0541 |

FOREIGN PATENT DOCUMENTS

| | | |
|---|---|---|
| WO | 2008036460 | 5/2008 |
| WO | 2011159923 | 12/2011 |
| WO | 2015034981 | 3/2015 |

OTHER PUBLICATIONS

International Application No. PCT/US2017/061464, "International Search Report and Written Opinion", dated Feb. 21, 2018, 12 pages.
PCT/US2017/061461, "International Preliminary Report on Patentability", dated May 23, 2018, 8 pages.
PCT/US2017/061461, "International Search Report and Written Opinion", dated Apr. 24, 2018, 11 pages.
PCT/US2017/061464, "International Preliminary Report on Patentability", dated May 23, 2019, 8 pages.
U.S. Appl. No. 15/811,766, "Non-Final Office Action", dated Oct. 4, 2019, 13 pages.

* cited by examiner

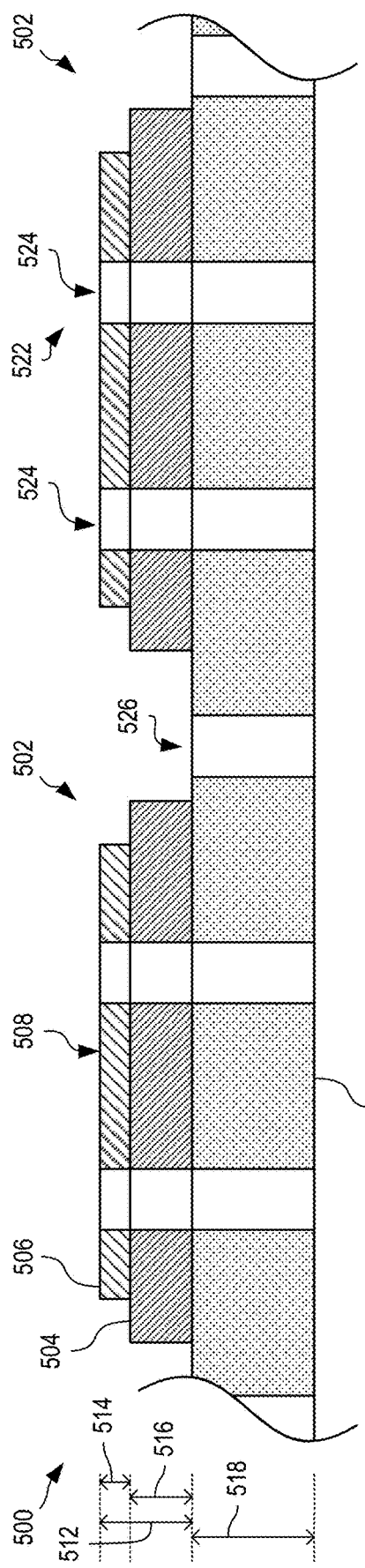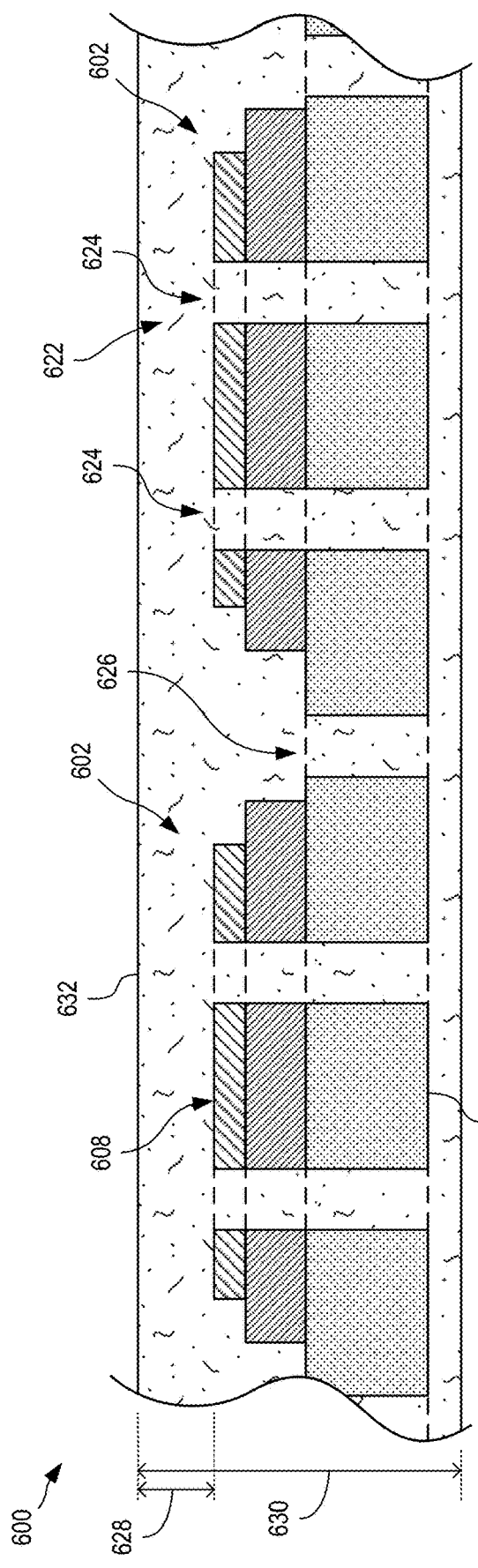

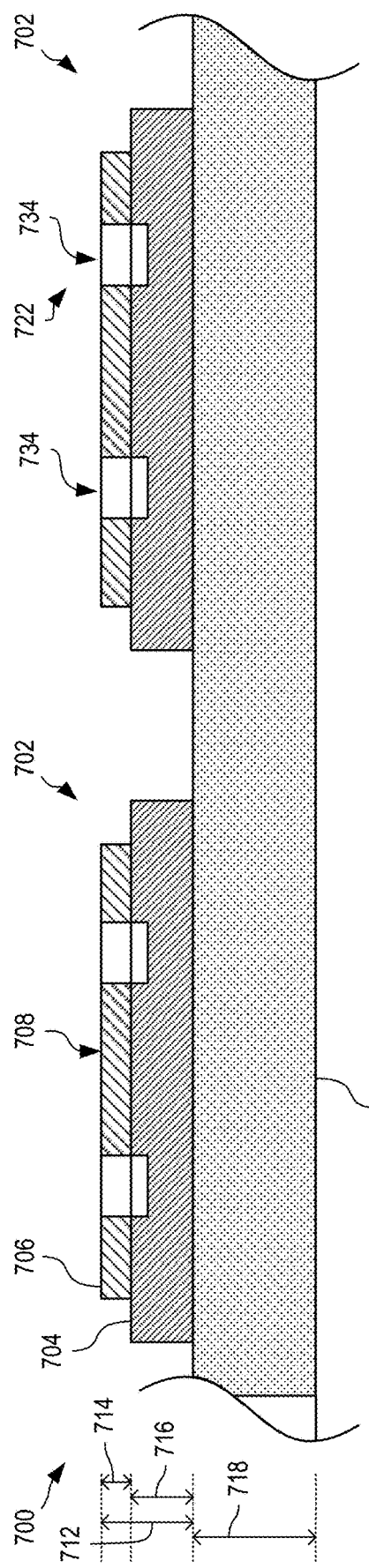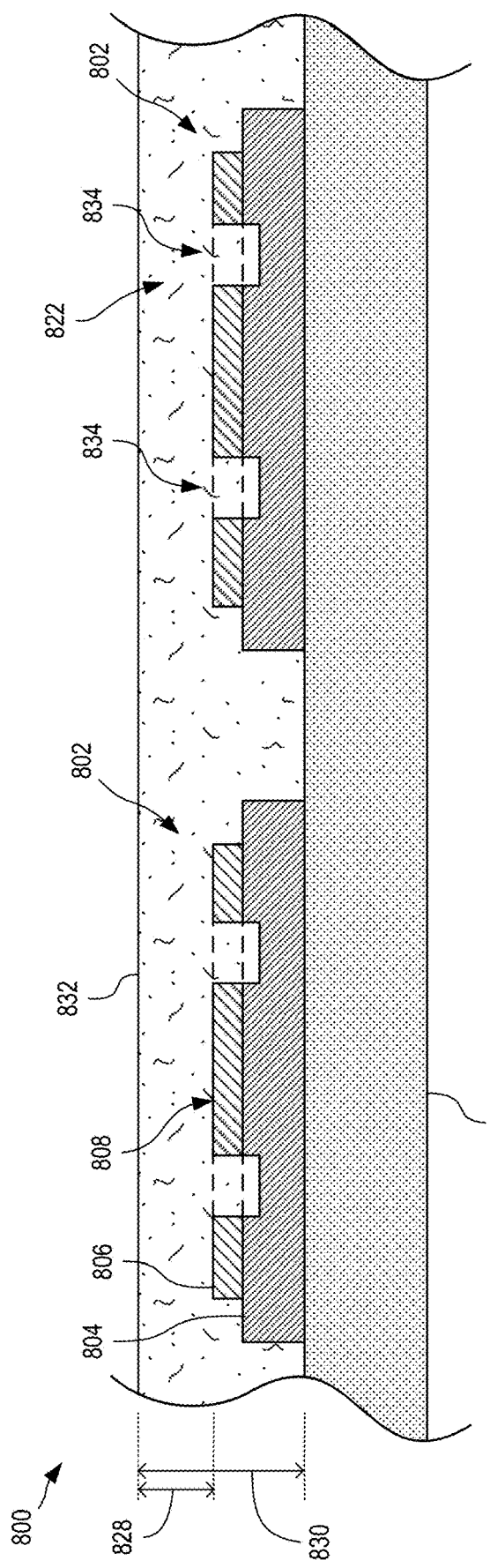

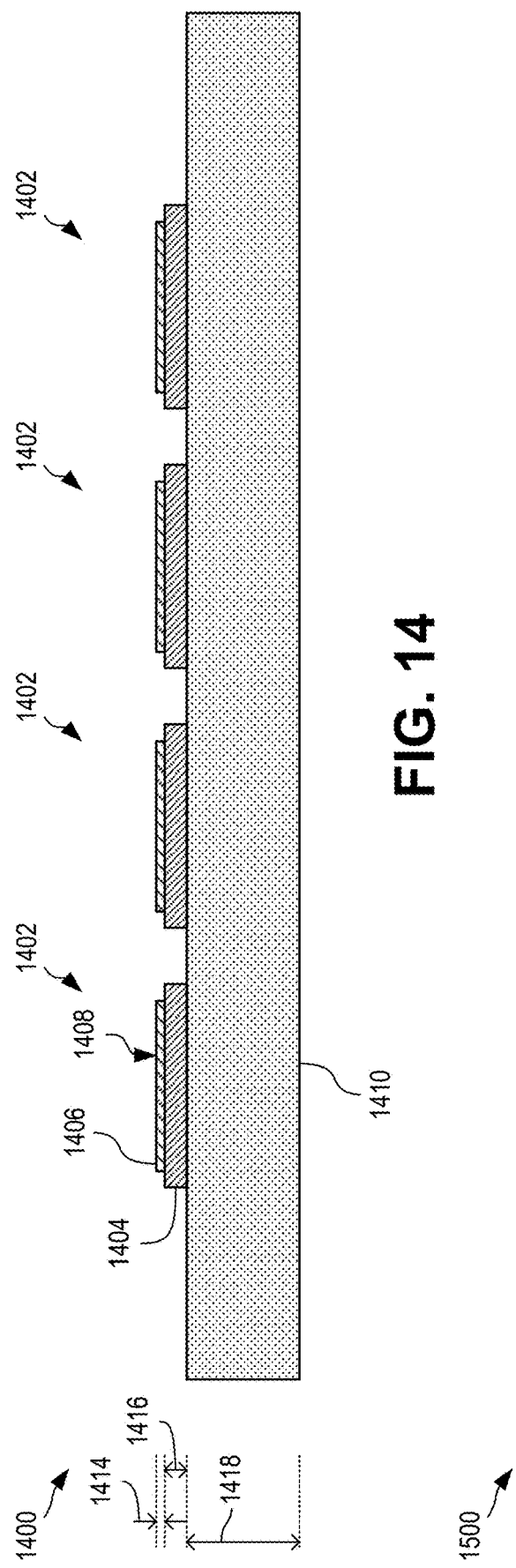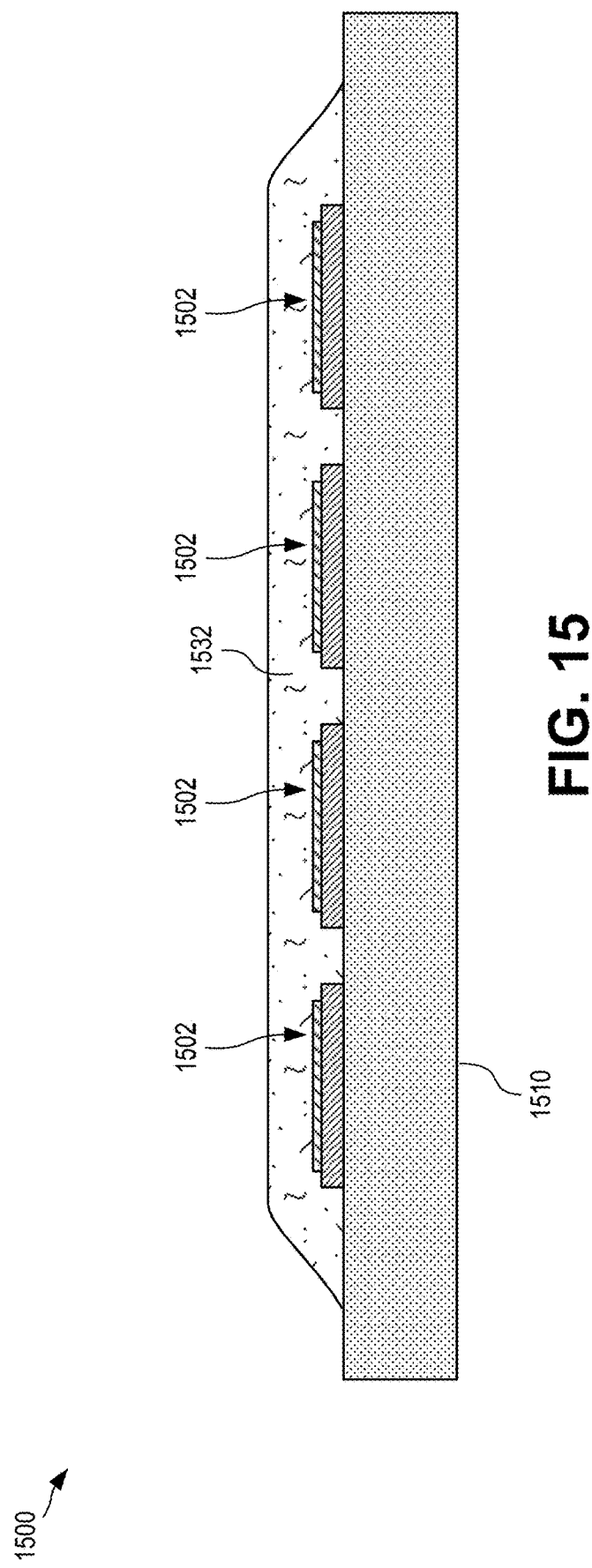

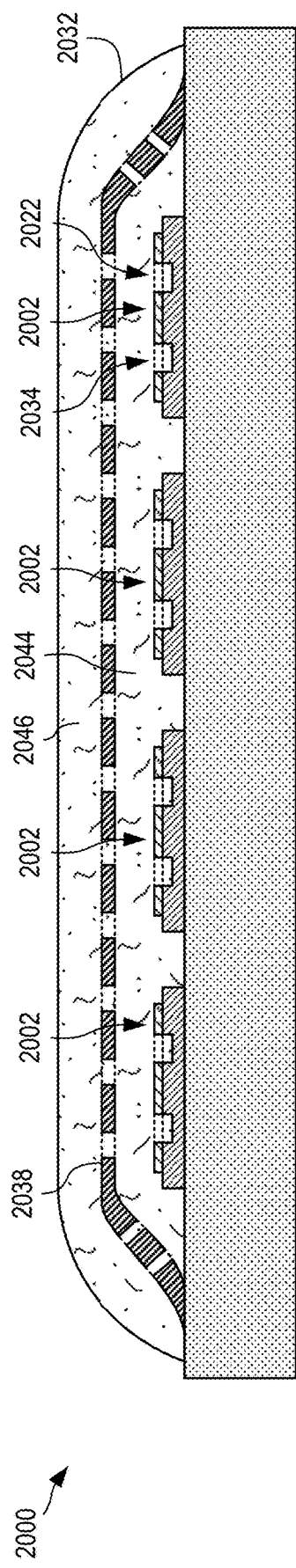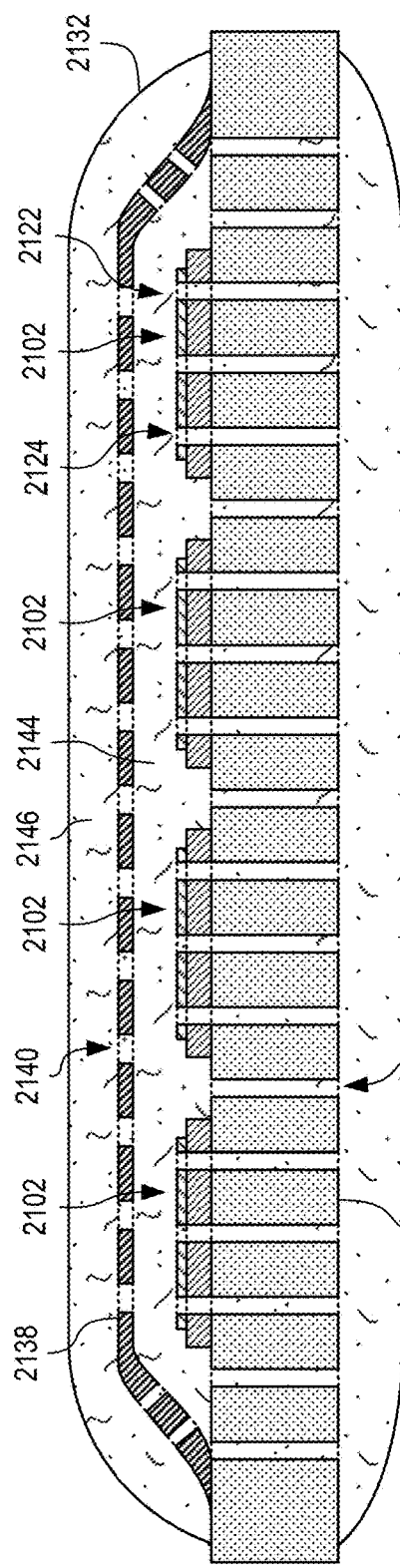

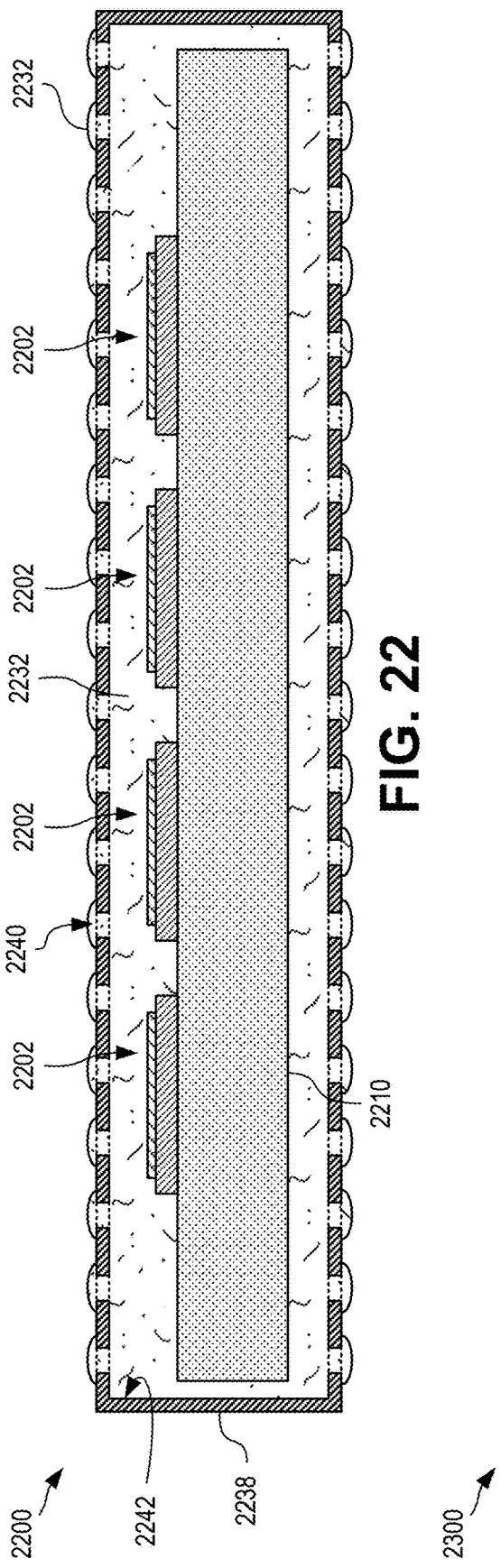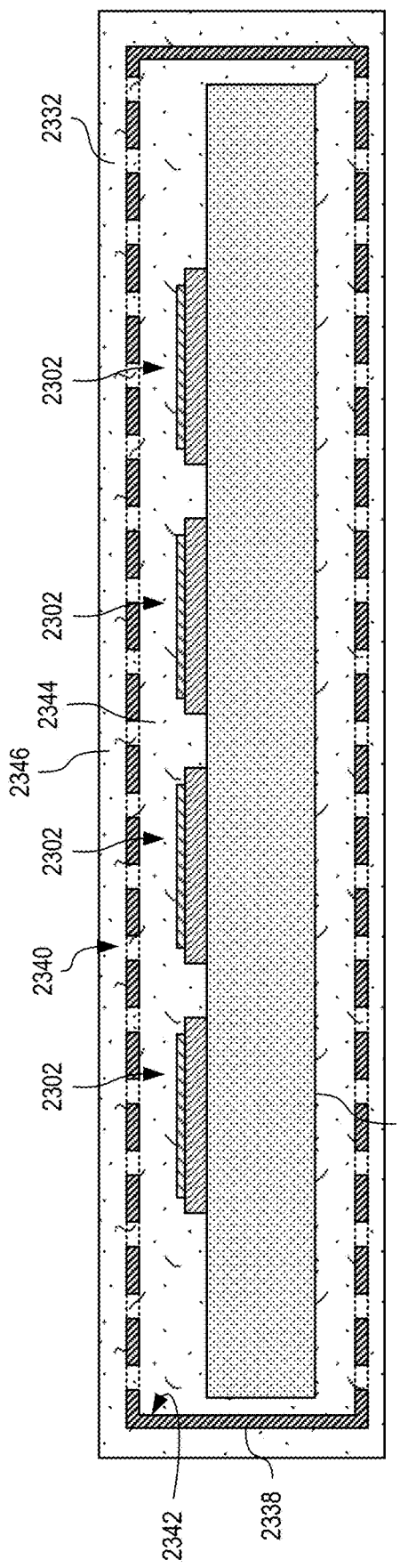

IMPLANTABLE ELECTRODES COMPRISING MECHANICALLY CONSTRAINED BIOCOMPATIBLE HYDROGELS WITH CONDUCTIVE PASSTHROUGH

CROSS REFERENCE TO RELATED APPLICATIONS

The present application claims the benefit of U.S. Provisional Application No. 62/421,702 filed Nov. 14, 2016 and entitled "IMPLANTABLE ELECTRODES COMPRISING MECHANICALLY CONS TRAINED BIOCOMPATIBLE HYDROGELS WITH CONDUCTIVE PASSTHROUGH," which is hereby incorporated by reference in its entirety.

TECHNICAL FIELD

The present disclosure relates to medical devices generally and more specifically to coatings for implantable electrodes.

BACKGROUND

Implantable electrodes can suffer from in vivo fouling, such as due to protein adsorption to the surface of the implantable electrodes. This initial protein adsorption can trigger the beginning of an inflammatory response, which may eventually culminate as fibrotic tissue deposition at the implant site. The fibrotic tissue deposition can act as a capacitive tissue layer and can consequently lead to a gradual increase in impedance over time as the tissue continues to build. As surrounding impedance increases, the implant becomes less efficient and may require more power to operate as desired. As a result, the efficacy and/or battery lifetime of the implant may be decreased and an implant user may require follow-up surgery to replace the fouled implant.

Efforts to decrease the in vivo impedance and increase the overall lifetime of the implant can include coating the electrode in a biomaterial that resists protein adsorption, however such biomaterials can be very difficult to reliable secure to or around an electrode. Attachment can be attempted using covalent bonding between the hydrogel and an oxide layer of the electrode. However, for certain electrodes, such as noble metals, robust covalent bonding can be very challenging to achieve. These materials may not easily form an oxide layer, without which the biomaterial has no functional handle on which to reliably, chemically attach. Unreliable attachment of biomaterials can result in further problems and can result in a lower effective lifespan of the implant than desired.

BRIEF DESCRIPTION OF THE DRAWINGS

The specification makes reference to the following appended figures, in which use of like reference numerals in different figures is intended to illustrate like or analogous components.

FIG. 5 is a partial cutaway view depicting an electrode array having anchoring features that are apertures according to certain aspects of the present disclosure.

FIG. 6 is a partial cutaway view depicting an electrode array having anchoring features that are apertures with applied hydrogel according to certain aspects of the present disclosure.

FIG. 7 is a partial cutaway view depicting an electrode array having anchoring features that are voids according to certain aspects of the present disclosure.

FIG. 8 is a partial cutaway view depicting an electrode array having anchoring features that are voids with applied hydrogel according to certain aspects of the present disclosure.

FIG. 14 is a cutaway view depicting an electrode array prior to hydrogel application according to certain aspects of the present disclosure.

FIG. 15 is a cutaway view depicting an electrode array with an applied hydrogel layer according to certain aspects of the present disclosure.

FIG. 20 is a cutaway view depicting an electrode array with hydrogel anchored using a non-swellable shell and void anchoring features of the electrodes according to certain aspects of the present disclosure.

FIG. 21 is a cutaway view depicting an electrode array with hydrogel anchored using a non-swellable shell and aperture anchoring features of the electrodes according to certain aspects of the present disclosure.

FIG. 22 is a cutaway view depicting an electrode array with hydrogel contained within a non-swellable shell according to certain aspects of the present disclosure.

FIG. 23 is a cutaway view depicting an electrode array with hydrogel contained within a non-swellable shell with an outer hydrogel layer according to certain aspects of the present disclosure.

DETAILED DESCRIPTION

Figure 1:
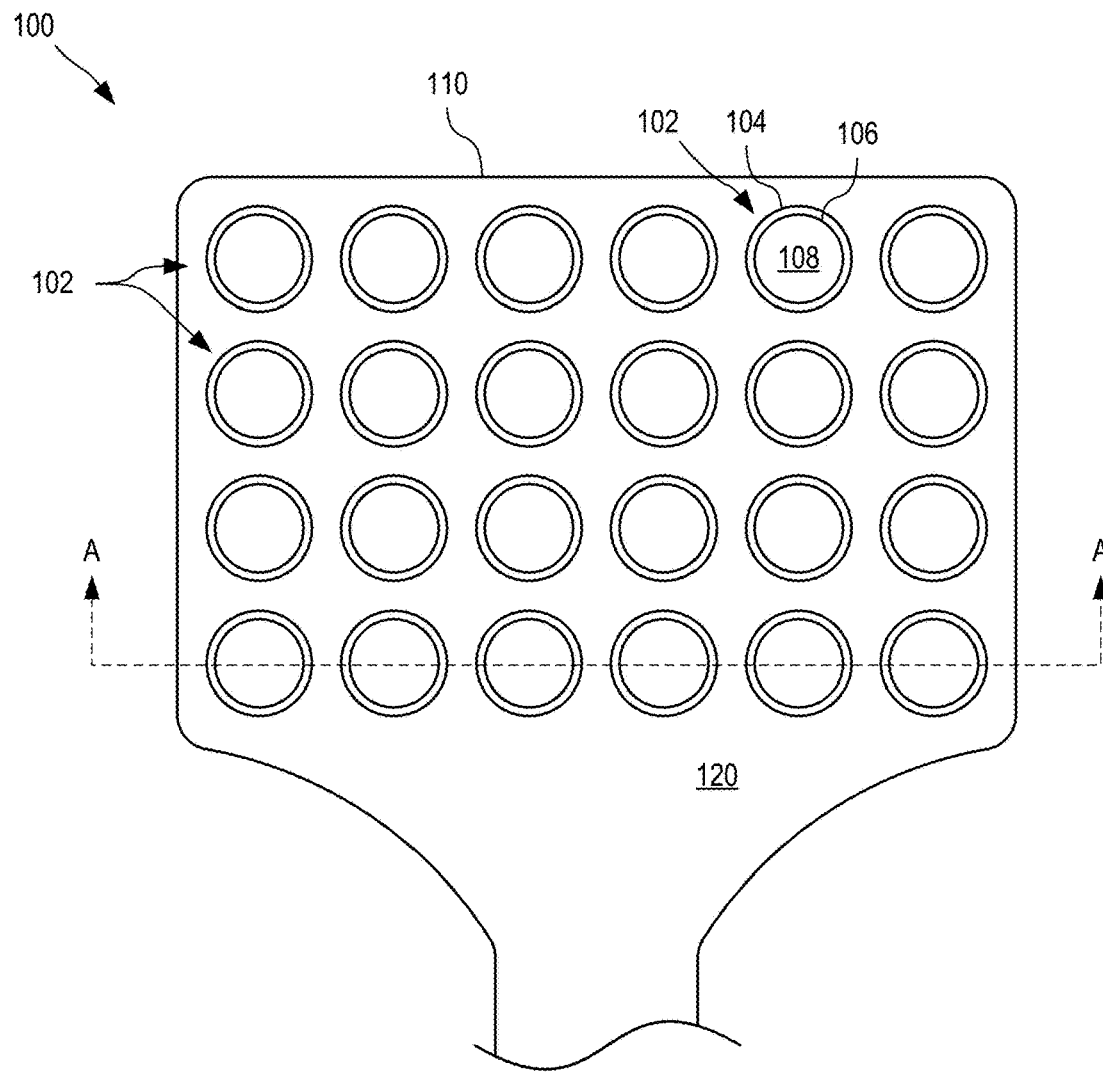
FIG. 1 is a top view of an electrode array prior to hydrogel application according to certain aspects of the present disclosure.

Certain aspects and features of the present disclosure relate to mechanically securing biomaterials, such as hydrogels, to an electrode of an implantable device. The hydrogel can be mechanically secured to an electrode via anchoring features of the electrode. Anchoring features can include apertures, voids, textures, or other patterns created in or on the electrode. The hydrogel can incorporate into the anchoring features to mechanically hold the hydrogel against the electrode. The anchoring features, by being located in or on the electrode, can further increase the surface area of the electrode that is exposed to the hydrogel, which can facilitate the conduction of electrical signals between the electrode and surrounding biological tissue. The substrate supporting the electrode can include additional anchoring features that further assist in mechanically securing the hydrogel.

The hydrogel can be mechanically secured to an electrode via anchoring features of the electrode. Anchoring features can include apertures, voids, textures, or other patterns created in or on the electrode. The hydrogel can incorporate into the anchoring features to mechanically hold the hydrogel against the electrode. The anchoring features, by being located in or on the electrode, can further increase the surface area of the electrode that is exposed to the hydrogel, which can facilitate the conduction of electrical signals between the electrode and surrounding biological tissue. The substrate supporting the electrode can include additional anchoring features that further assist in mechanically securing the hydrogel.

In some cases, a flexible electrode array can include multiple electrodes. Anchoring features can be created by perforating the electrodes to create apertures. Any suitable method can be used to perforate the electrodes, such as mechanical drilling, laser drilling, laser cutting, laser ablation, or other suitable techniques. In some cases, anchoring features, such as apertures, can be formed during formation of the electrodes, such as through masking techniques. Anchoring features, such as apertures, can also be created in the substrate as well as the electrodes. A hydrogel coating precursor can be applied to the outward facing surfaces of the electrodes, and optionally substrates, as well as on the inner surfaces of the anchoring features (e.g., apertures). While apertures are described above, other anchoring features can be used, such as voids, blind holes (e.g., not through holes), hot embossing, cold embossing, bead blasting, or any other technique for creating anchoring features or increasing the surface roughness of the electrode. In some cases, an anchoring feature can be an opening that extends any depth into the electrode, such as an aperture extending through the electrode thickness or a void that extends partially through the electrode thickness. In some instances, the hydrogel coating may only be selectively applied to certain portions of the electrode array assembly (e.g. directly over one or more of the electrodes).

In some cases, the metal electrodes can be fabricated to include anchoring features. Such electrodes can take the form of mesh-like metal structures. In this manner, the starting seed metal may be patterned, for example with photolithography, and then the seed pattern mesh may be plated up to the specified thickness. In a subtractive process, a full-thickness metal may be clad onto the substrate, a high-aspect ratio electrode pattern may be defined photolithographically to the metal, the metal etched to form the mesh, and the photoresist layer removed. In any case, a variety of approaches can be used to physically anchor and/or entrap an applied hydrogel precursor so that it the hydrogel is substantially affixed to the electrode using mechanical anchoring without the need to rely primarily on covalently bonding the hydrogel to the metal. Once a hydrogel precursor is applied, it may be cross-linked in place using a flood ultraviolet (UV) system, if UV-curable, or any other suitable technique (e.g., heating to initiate a thermal polymerization of the precursor).

Certain aspects and features of the present disclosure relate to mechanically securing biomaterials, such as hydrogels, to an electrode of an implantable device using a non-swellable shell. Hydrogel can be applied to an electrode surface and then mechanically constrained in place by a non-swellable shell. The non-swellable material can be secured to a substrate supporting an electrode or can otherwise surround an electrode and the hydrogel. The non-swellable shell can include openings or passthroughs that allow for electrical conduction across the non-swellable shell. The hydrogel can extend out of the openings to contact adjacent biological tissue. In some cases, an outer layer of hydrogel can surround the non-swellable shell and connected to the inner layer of hydrogel through the openings of the non-swellable shell.

In some cases, biocompatible hydrogels may be mechanically affixed to the electrode array using a non-swellable shell. In this approach, after a first hydrogel layer is applied to the electrode array, a non-swellable and patternable secondary coating can be applied. This second, non-swellable coating can further restrict movement and/or delamination of the hydrogel from the electrode array. Any suitable non-swellable material, conformal, or biocompatible coating may be used, such as parylene C or any of the other parylene vapor deposition polymers. In cases where the hydrogel may be selectively applied to the electrode array (e.g. just over the electrode metal), existing techniques to adhere the non-swellable material (e.g., parylene) to the substrate of the electrode array can be employed, such as any suitable primer or pre-treatment to assist in chemically anchoring the non-swellable material to the substrate. While the non-swellable material may be chemically anchored to the substrate, the hydrogel layer may not necessarily be chemically anchored to the electrodes and rather may be mechanically held in place due to physical interaction with the non-swellable material. Once the non-swellable material is in place, various openings or apertures may be created in the non-swellable material through any suitable technique, such as laser ablation, mechanical drilling, milling, inductively coupled plasma (ICP) etching, or any other convenient fabrication technique. The openings may allow the hydrogel to at least partially swell up through the openings. In some cases, an additional layer of hydrogel precursor can be applied over the non-swellable material. This additional layer may entangle or otherwise form an interpenetrating network with the first layer of hydrogel through the openings in the non-swellable material, thereby locking it in place. Such a secondary hydrogel coating may improve overall fouling resistance of the electrode array and may lead to better overall performance and biocompatibility.

Certain aspects and features of the present disclosure may be especially suitable for securing biomaterials (e.g., hydrogels) to electrodes made of noble metals (e.g., platinum, gold, and palladium). In some cases, the electrodes may specifically be made of platinum or gold. Platinum or gold can be especially useful as an implantable electrode due to their high biocompatibility and ability to be surface roughened. Metal electrodes and/or electrode arrays may be fabricated in any suitable geometries. Electrodes may be fabricated on thin, flexible substrates, such as polyimide, or a liquid crystal polymer (LCP).

As used herein, references are made to securing hydrogels to electrodes, however various aspects and features the present disclosure may involve securing other biomaterials to electrodes, such as brush layers, semi-interpenetrating networks, or other natural and/or synthetic polymeric compositions. The biomaterials can be electrically conductive, such as being naturally conductive or including conductive materials incorporated therein. For example, biomaterials can include a sufficient concentration of dissolved ions suitable for providing desired electrical conductivity. Any suitable hydrogel can be used, such as a cross-linked polyethylene glycol (PEG) diacrylate. As used herein, the term hydrogel may refer to a hydrogel precursor or a hydrogel, as appropriate.

In some cases, a non-swelling or low-swelling hydrogel can be uses. In some cases, a polymerizable hydrogel precursor may contain a non-reactive diluent (e.g., glycol ethers or alcohols), which can displace a volume equal to or approximately equal to the volume of physiological fluid that would ultimately swell the biocompatible hydrogel in vivo. In this manner, the swelling forces of the biocompatible hydrogel may be controlled to limit delamination of the hydrogel coating from the electrode array.

Certain aspects and features the present disclosure allow hydrogels to be mechanically secured to electrodes without the need to rely on covalent bonding between the hydrogel and the electrode. Such mechanical bonding can provide for a more robust and reliable attachment of the hydrogel to the electrode, especially for electrodes made of noble metals. Using the techniques disclosed herein, an implant can include desirable electrode materials (e.g., noble metals) and still retain the benefit of hydrogel coatings (e.g., improved biocompatibility) that would otherwise normally be very difficult to achieve with desirable electrode materials.

The improved ability to secure the hydrogel to an electrode using the techniques disclosed herein can allow the electrode to remain implanted for longer with no or fewer negative side effects. By reducing the amount of fibrotic response around an implant using the techniques described herein, the implant may be able to continue functioning without needing to compensate for otherwise expected increases in surrounding impedance that would have otherwise occurred due to fibrotic response. Thus, the implant may be able to function for longer on the same power supply or function similarly using a smaller power supply. An implant using certain aspects and features of the present disclosure may operate for a longer lifetime than previously possible, such as 10 or 20 years, thus decreasing the need for subsequent follow-up surgeries for a user.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale. Specifically, various elements of the figures may be shown in exaggerated dimensions for explanatory purposes.

FIG. 1 is top view of an electrode array 100 prior to hydrogel application according to certain aspects of the present disclosure. The electrode array 100 can include a plurality of electrodes 102, although in some cases an array may include only a single electrode. Each electrode 102 can include a base layer 104 and an upper layer 106, although in some cases an electrode 102 can include only a single layer of metal or more than two layers of metal. In some cases, the base layer 104 and upper layer 106 can be different metals, such as a base layer 104 of gold and an upper layer 106 of platinum (e.g., platinum iridium). As used herein, reference to metals used to form an electrode 102 includes suitable alloys of those metals (e.g., platinum can refer to a platinum iridium alloy). Each electrode 102 can have an upper surface 108. While the base layer 104 is depicted as larger in diameter than the upper layer 106, that need not be the case and each layer can be any suitable size. The electrodes 102 of electrode array 100 are depicted as circular in shape, however any suitable shaped electrodes may be used, such as square, hexagonal, or others. The spacing of electrodes can be densely and regularly spaced with or without gaps in-between.

The electrodes 102 of the electrode array 100 can be supported on a substrate 110. The electrodes 102 can be coupled to the substrate in any suitable manner, such as formed on the substrate 110, attached to the substrate 110, or embedded within the substrate 110. The substrate 110 can have an upper surface 120 to which the electrodes 102 are coupled, although electrodes 102 can be coupled to more than one surface of the substrate 110 in some cases. Electrical conductors (e.g., wires) can be embedded within the substrate 110 and connect the electrodes 102 to other equipment, such as a controller of an implant.

Electrodes 102 of electrode array 110 are depicted in a repeating pattern, however any number of electrodes 102 may be positioned in any suitable fashion on the electrode array 110, including randomly.

Figure 2:
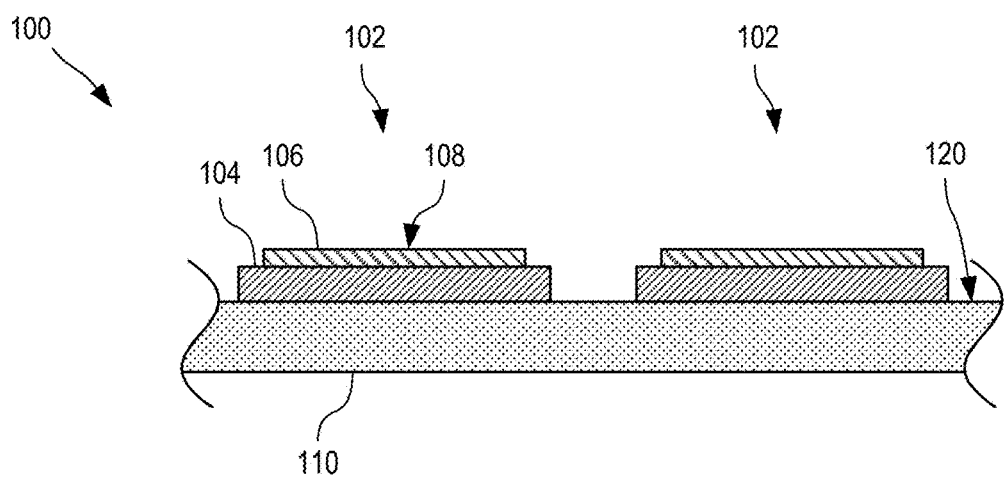
FIG. 2 is a partial cutaway view of the electrode array of FIG. 1 taken along line A:A according to certain aspects of the present disclosure.

FIG. 2 is a partial cutaway view of the electrode array 100 of FIG. 1 taken along line A:A according to certain aspects of the present disclosure. The substrate 110 can support the electrodes 102 on its top surface 120. Each electrode 102 can include a base layer 104 supporting an upper layer 106 having an upper surface 108.

Figure 3:
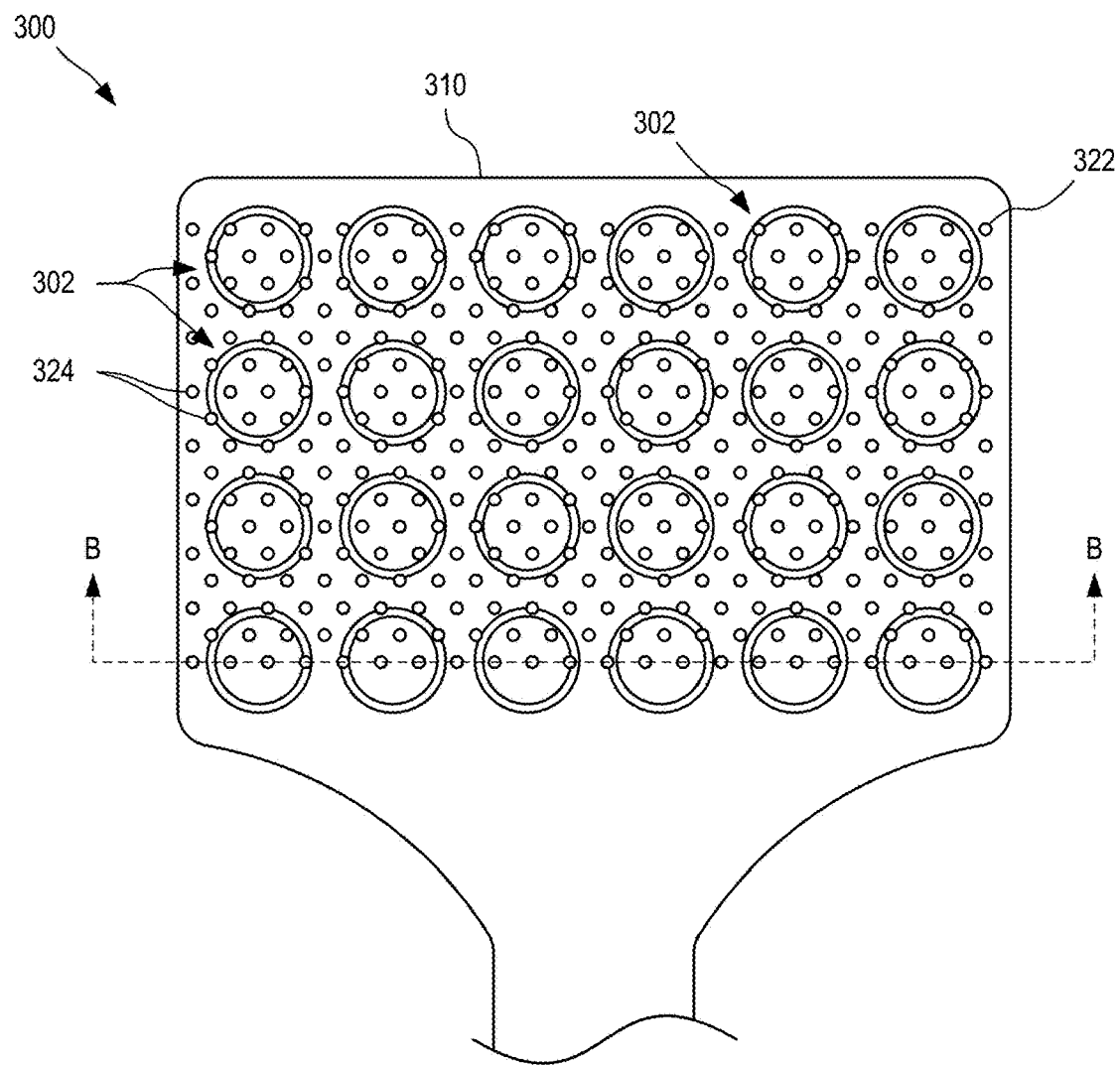
FIG. 3 is top view of an electrode array having anchoring features according to certain aspects of the present disclosure.

FIG. 3 is top view of an electrode array 300 having anchoring features 322 according to certain aspects of the present disclosure. The electrode array 300 can be the electrode array 100 of FIG. 1 after anchoring features 322 have been formed thereon (e.g., through mechanical drilling or laser ablation). The anchoring features 322 can include a plurality of apertures 324 created through the electrodes 302. In some cases, apertures 324 can also be created through the substrate 310.

Figure 4:
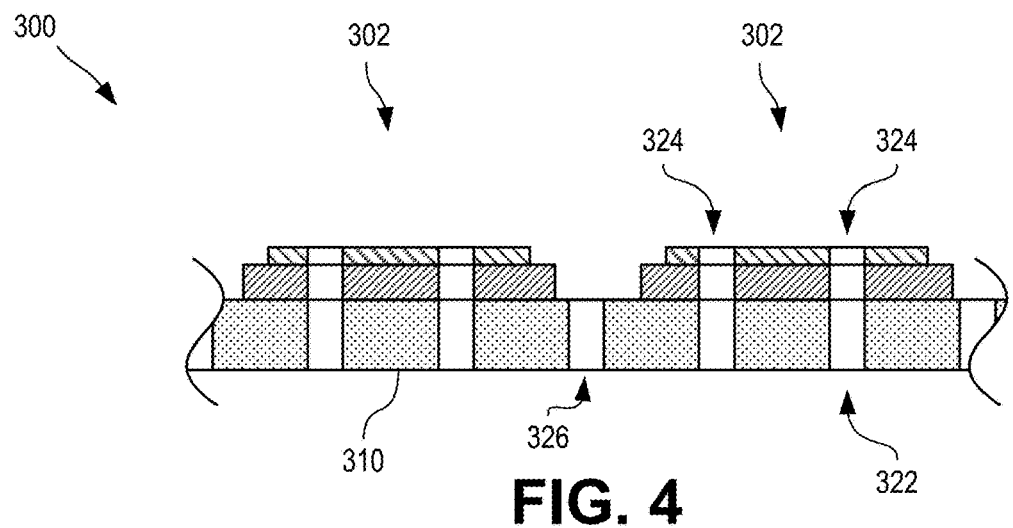
FIG. 4 is a partial cutaway view of the electrode array of FIG. 3 taken along line B:B according to certain aspects of the present disclosure.

FIG. 4 is a partial cutaway view of the electrode array 300 of FIG. 3 taken along line B:B according to certain aspects of the present disclosure. The electrode array 300 can include multiple anchoring features 322. The electrode array 300 can include a one or more apertures 324 passing through each electrode 302. In some cases, the apertures 324 can also pass through the substrate 310. In some cases, one or more additional anchoring features 326 can occur on the substrate 310 and not on the electrodes 302. The additional anchoring feature 326 can be an aperture that passes through the substrate 310, but not the electrodes 302.

FIG. 5 is a partial cutaway view depicting an electrode array 500 having anchoring features 522 that are apertures 524 according to certain aspects of the present disclosure. The electrode array 500 can be electrode array 300 of FIG. 3. The electrode array 500 can include one or more electrodes 502 supported by a substrate 510. The electrodes 502 can include a base layer 504 and an upper layer 506. The electrodes 502 can have a thickness 512. Any suitable thickness 512 can be used, such as thickness between about 3 microns to about 6 microns, although other thicknesses can be used, including less than 3 microns and greater than 6 microns. In some cases, the base layer 504 can have a thickness 516 that is about three to about five microns in thickness, although other values can be used. In some cases, the upper layer 506 can have a thickness 514 that is about 0.5 to about 1 micron in thickness, although other values can be used. In some cases, the base layer 504 of made of gold or a gold alloy and the upper layer 506 is made of platinum or a platinum alloy. The electrodes 502 can have any suitable dimensions, such as about 500 microns to about 2 mm in diameter, although other sizes can be used.

Apertures 524 can be formed in the electrodes 502, such as using any suitable technique. The apertures 524 can be any suitable size, such as approximately 5 microns to approximately 50 microns, although other ranges may be used. An aperture 524 can be an opening that extends entirely through a material. As used herein, aperture 524 extends through the electrode 502. Apertures 524 also happen to extend through the substrate 510, although that need not always be the case. In some cases, additional anchoring features 526 can include apertures passing through the substrate 510 at locations not occupied by an electrode 502. The substrate 510 can have a thickness 518 of any suitable size. In some cases, substrate 510 is thin and flexible to facilitate maneuverability and implantation of the electrode array 500.

FIG. 6 is a partial cutaway view depicting an electrode array 600 having anchoring features 622 that are apertures 626 with applied hydrogel 632 according to certain aspects of the present disclosure. The electrode array 600 can be the electrode array 500 of FIG. 5 after hydrogel 632 has been applied thereto. The hydrogel 632 can be placed over the electrodes 602 and optionally over the substrate 610. The hydrogel 632 can be introduced into the anchoring features 622 of the electrodes 602 (e.g., apertures 624), optionally including any additional anchoring features 626 of the substrate 610. The hydrogel 632 can have a total thickness 630 and an over-electrode thickness 628. The over-electrode thickness 628 can represent a minimum, maximum, or average thickness of the hydrogel 632 as measured from the top surface 608 of an electrode 602. The over-electrode thickness 628 of the hydrogel 632 can be any suitable thickness, such as about 10 microns to about 100 microns, although other ranges can be used. In some cases, the over-electrode thickness 628 of the hydrogel 632 is in the tens of microns.

FIG. 7 is a partial cutaway view depicting an electrode array 700 having anchoring features 722 that are voids 734 according to certain aspects of the present disclosure. The electrode array 700 can be electrode array 100 of FIG. 1 after anchoring features 722 have been applied thereto. The electrode array 700 can include one or more electrodes 702 supported by a substrate 710. The electrodes 702 can include a base layer 704 and an upper layer 706. The electrodes 702 can have a thickness 712. Any suitable thickness 712 can be used, such as thickness between about 3 microns to about 6 microns, although other thicknesses can be used, including less than 3 microns and greater than 6 microns. In some cases, the base layer 704 can have a thickness 716 that is about three to about five microns in thickness, although other values can be used. In some cases, the upper layer 706 can have a thickness 714 that is about 0.5 to about 1 micron in thickness, although other values can be used. In some cases, the base layer 704 of made of gold or a gold alloy and the upper layer 706 is made of platinum or a platinum alloy. The electrodes 702 can have any suitable dimensions, such as about 700 microns to about 2 mm in diameter, although other sizes can be used.

Voids 734 can be formed in the electrodes 702, such as using any suitable technique. The voids 734 can be any suitable size, such as approximately 5 microns to approximately 50 microns, although other ranges may be used. A void 734 can extend partially into a material (e.g., into an electrode 702) without extending fully through the material. As used herein, void 734 extends into at least a portion of electrode 702. Void 734 can extend partially or fully through the thickness 714 of the upper layer 706 and may optionally extend partially through the thickness 716 of the base layer 704. Any suitable technique can be used to create the voids 734, such as laser ablation. In some cases, voids can also be formed in the substrate 710 to act as additional anchoring features. The substrate 710 can have a thickness 718 of any suitable size. In some cases, substrate 710 is thin and flexible to facilitate maneuverability and implantation of the electrode array 700.

FIG. 8 is a partial cutaway view depicting an electrode array 800 having anchoring features 822 that are voids 834 with applied hydrogel 832 according to certain aspects of the present disclosure. The electrode array 800 can be the electrode array 700 of FIG. 7 after hydrogel 832 has been applied thereto. The hydrogel 832 can be placed over the electrodes 802 and optionally over the substrate 810. The hydrogel 832 can be introduced into the anchoring features 822 of the electrodes 802 (e.g., voids 834), optionally including any additional anchoring features of the substrate 810. The hydrogel 832 can have a total thickness 830 and an over-electrode thickness 828. The over-electrode thickness 828 can represent a minimum, maximum, or average thickness of the hydrogel 832 as measured from the top surface 808 of an electrode 802. The over-electrode thickness 828 of the hydrogel 832 can be any suitable thickness, such as about 10 microns to about 100 microns, although other ranges can be used. In some cases, the over-electrode thickness 828 of the hydrogel 832 is in the tens of microns.

Figure 9:
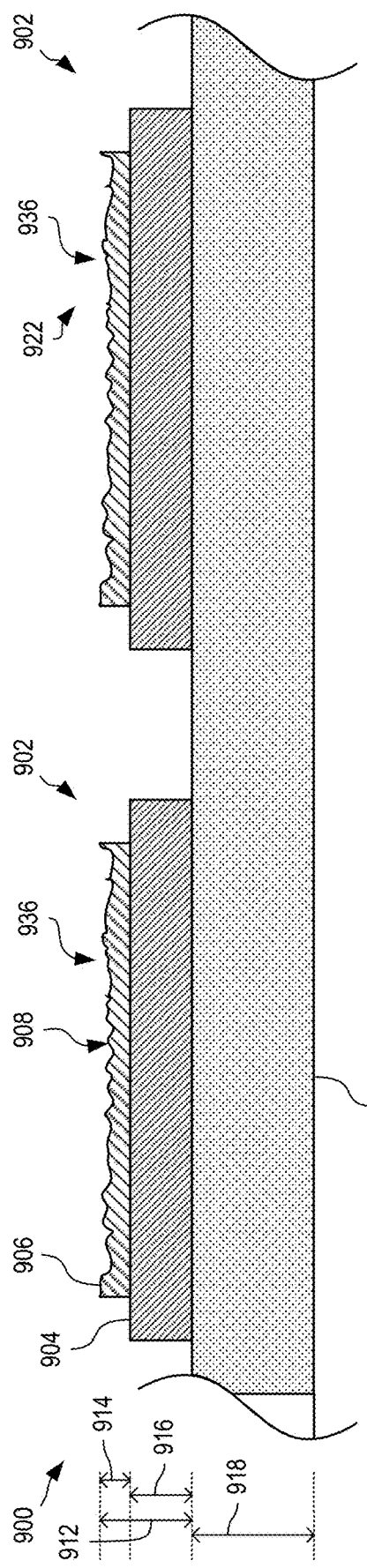
FIG. 9 is a partial cutaway view depicting an electrode array having anchoring features that are surface textures according to certain aspects of the present disclosure.

FIG. 9 is a partial cutaway view depicting an electrode array having anchoring features 922 that are surface textures 936 according to certain aspects of the present disclosure. The electrode array 900 can be electrode array 100 of FIG. 1 after anchoring features 922 have been applied thereto. The electrode array 900 can include one or more electrodes 902 supported by a substrate 910. The electrodes 902 can include a base layer 904 and an upper layer 906. The electrodes 902 can have a thickness 912. Any suitable thickness 912 can be used, such as thickness between about 3 microns to about 6 microns, although other thicknesses can be used, including less than 3 microns and greater than 6 microns. In some cases, the base layer 904 can have a thickness 916 that is about three to about five microns in thickness, although other values can be used. In some cases, the upper layer 906 can have a thickness 914 that is about 0.5 to about 1 micron in thickness, although other values can be used. In some cases, the base layer 904 of made of gold or a gold alloy and the upper layer 906 is made of platinum or a platinum alloy. The electrodes 902 can have any suitable dimensions, such as about 900 microns to about 2 mm in diameter, although other sizes can be used.

Surface textures 936 can be formed in the electrodes 902, such as using any suitable technique. The surface textures 936 can increase the average roughness of the upper surface 908 of the electrodes 902. The surface textures 936 can have any suitable precision, such as precision from approximately 5 microns to approximately 50 microns, although other ranges may be used. A surface texture 936 can include elements that extend partially into the upper layer 906 of the electrode 902. Any suitable technique can be used to create the surface textures 936, such as laser ablation or electrical discharge texturing. In some cases, surface textures can also be formed in the substrate 910 to act as additional anchoring features. The substrate 910 can have a thickness 918 of any suitable size. In some cases, substrate 910 is thin and flexible to facilitate maneuverability and implantation of the electrode array 900.

Figure 10:
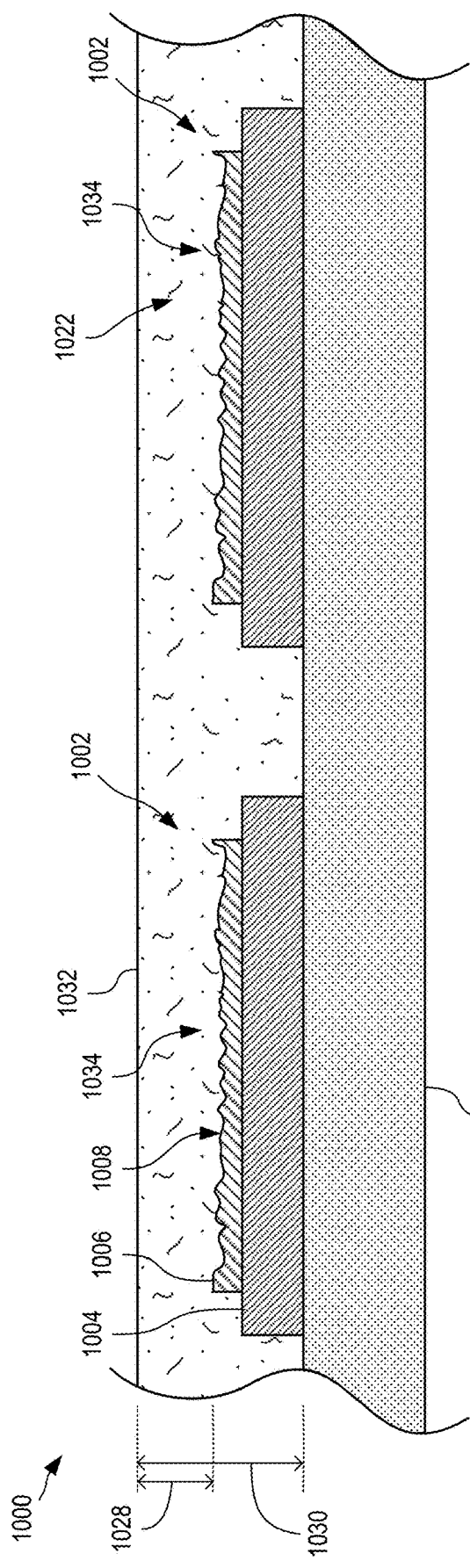
FIG. 10 is a partial cutaway view depicting an electrode array having anchoring features that are surface textures with applied hydrogel according to certain aspects of the present disclosure.

FIG. 10 is a partial cutaway view depicting an electrode array 1000 having anchoring features 1022 that are surface textures 1034, the electrode array 1000 including applied hydrogel 1032 according to certain aspects of the present disclosure. The electrode array 1000 can be the electrode array 900 of FIG. 9 after hydrogel 1032 has been applied thereto. The hydrogel 1032 can be placed over the electrodes 1002 and optionally over the substrate 1010. The hydrogel 1032 can be introduced into the anchoring features 1022 of the electrodes 1002 (e.g., surface textures 1036), optionally including any additional anchoring features of the substrate 1010. The hydrogel 1032 can have a total thickness 1030 and an over-electrode thickness 1028. The over-electrode thickness 1028 can represent a minimum, maximum, or average thickness of the hydrogel 1032 as measured from the top surface 1008 of an electrode 1002. The over-electrode thickness 1028 of the hydrogel 1032 can be any suitable thickness, such as about 10 microns to about 100 microns, although other ranges can be used. In some cases, the over-electrode thickness 1028 of the hydrogel 1032 is in the tens of microns.

Figure 11:
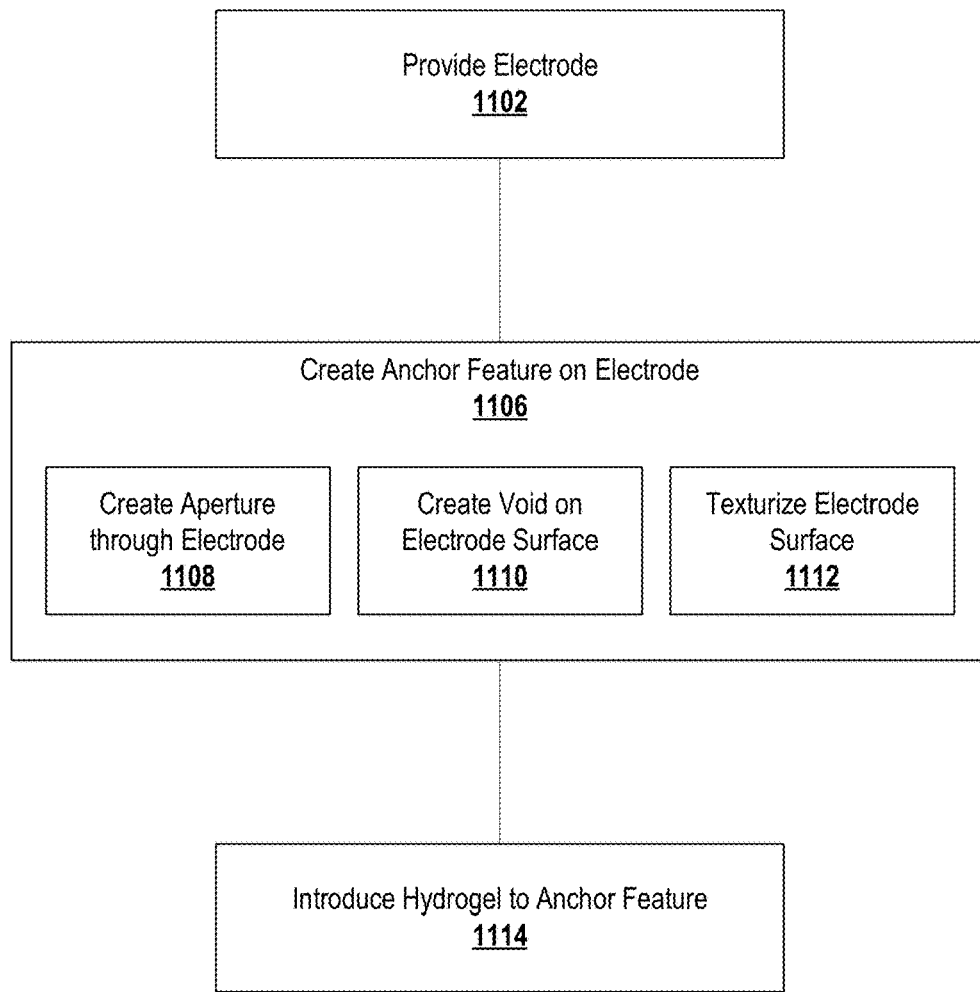
FIG. 11 is a flowchart depicting a process for mechanically securing hydrogel to an electrode using anchoring features according to certain aspects of the present disclosure.

FIG. 11 is a flowchart depicting a process 1100 for mechanically securing hydrogel to an electrode using anchoring features according to certain aspects of the present disclosure. At block 1102, an electrode can be provided. In some cases, the electrode can be pre-manufactured. In some cases, the electrode can be fabricated on a substrate. At block 1106, an anchoring feature can be created on the electrode. Any suitable anchoring feature can be created. Creating an anchoring feature can include creating an aperture through the electrode at block 1108, creating a void on the electrode surface at block 1110, or texturizing the electrode surface at block 1112. In some cases, creating an anchor feature at block 1106 can include any combination of block 1108, block 1110, and block 1112. In some cases, other anchoring features can be created at block 1106. At block 1114, hydrogel is introduced to the anchoring feature. At block 1114, hydrogel can also be introduced to the electrode and optionally the substrate. In some cases, introducing hydrogel at block 1114 includes introducing a hydrogel precursor. In some cases, introducing hydrogel at block 1114 can include pre-swelling the hydrogel, such as with a material selected to be offset by physiological fluids when the implant is implanted.

Figure 12:
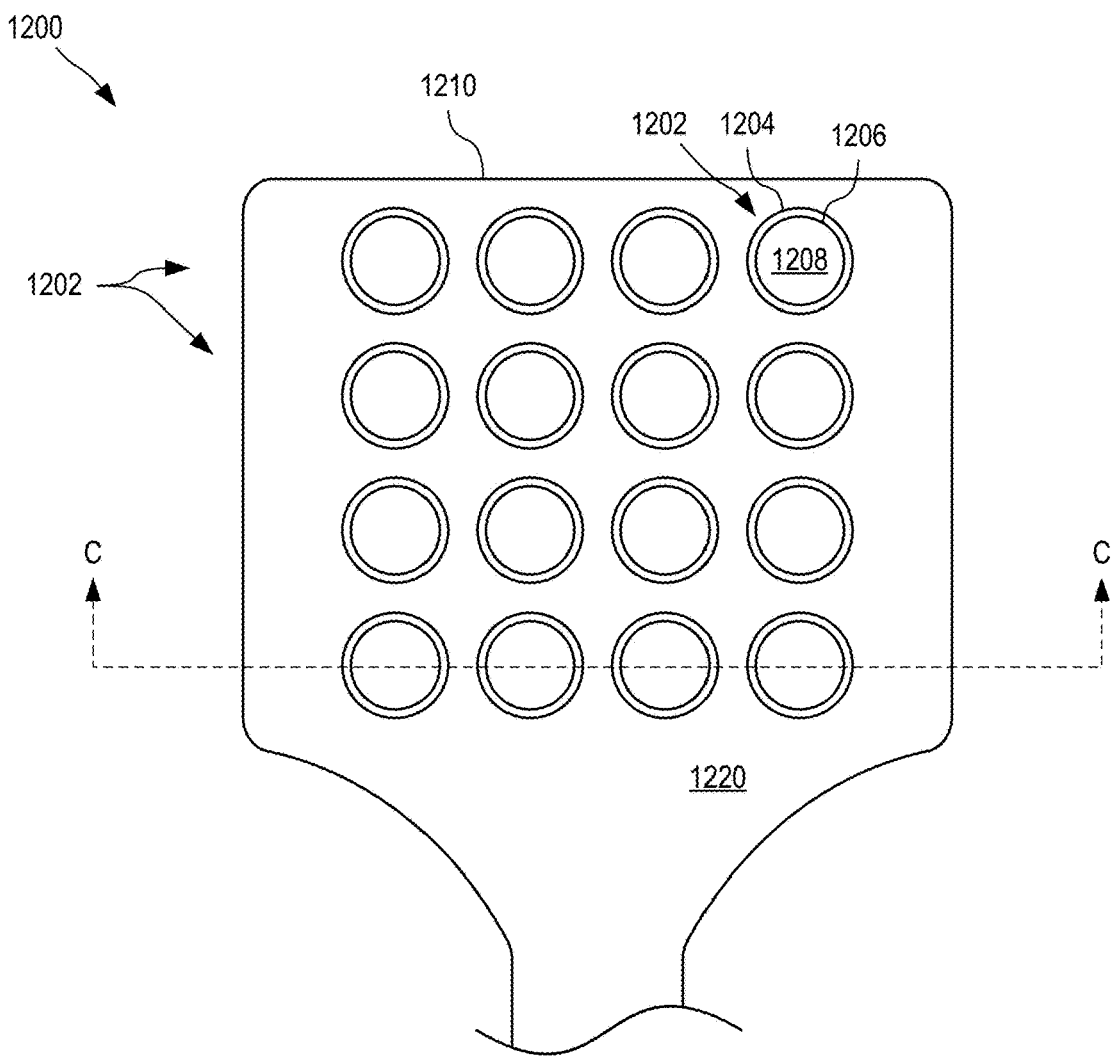
FIG. 12 is top view of an electrode array prior to hydrogel application according to certain aspects of the present disclosure.

FIG. 12 is top view of an electrode array 1200 prior to hydrogel application according to certain aspects of the present disclosure. The electrode array 1200 can include a plurality of electrodes 1202, although in some cases an array may include only a single electrode. Each electrode 1202 can include a base layer 1204 and an upper layer 1206, although in some cases an electrode 1202 can include only a single layer of metal or more than two layers of metal. In some cases, the base layer 1204 and upper layer 1206 can be different metals, such as a base layer 1204 of gold and an upper layer 1206 of platinum (e.g., platinum iridium). As used herein, reference to metals used to form an electrode 1202 includes suitable alloys of those metals (e.g., platinum can refer to a platinum iridium alloy). Each electrode 1202 can have an upper surface 1208. While the base layer 1204 is depicted as larger in diameter than the upper layer 1206, that need not be the case and each layer can be any suitable size. The electrodes 1202 of electrode array 1200 are depicted as circular in shape, however any suitable shaped electrodes may be used, such as square.

The electrodes 1202 of the electrode array 1200 can be supported on a substrate 1210. The electrodes 1202 can be coupled to the substrate in any suitable manner, such as formed on the substrate 1210, attached to the substrate 1210, or embedded within the substrate 1210. The substrate 1210 can have an upper surface 1220 to which the electrodes 1202 are coupled, although electrodes 1202 can be coupled to more than one surface of the substrate 1210 in some cases. Electrical conductors (e.g., wires) can be embedded within the substrate 1210 and connect the electrodes 1202 to other equipment, such as a controller of an implant.

Electrodes 1202 of electrode array 1210 are depicted in a repeating pattern, however any number of electrodes 1202 may be positioned in any suitable fashion on the electrode array 1210, including randomly.

Figure 13:
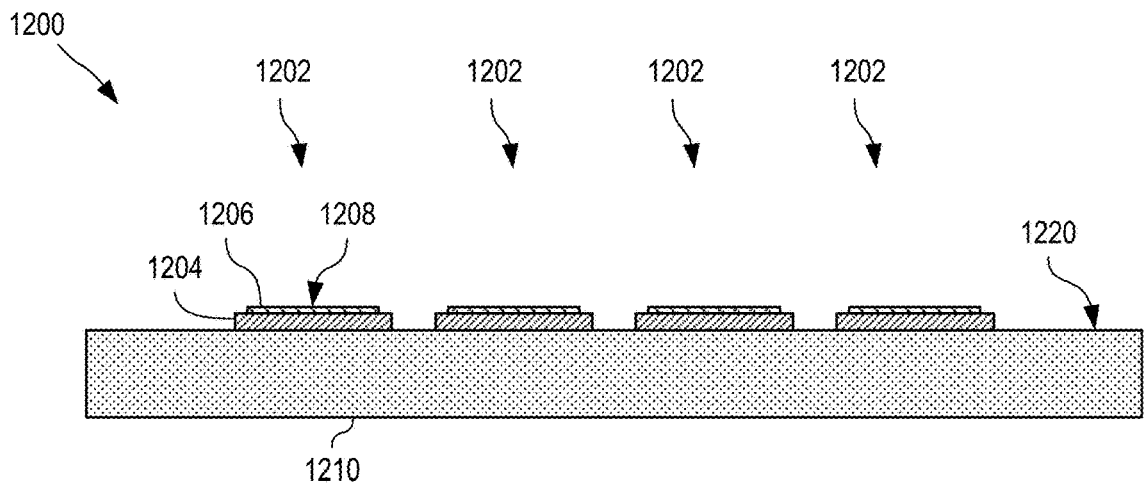
FIG. 13 is a cutaway view of the electrode array of FIG. 12 taken along line C:C according to certain aspects of the present disclosure.

FIG. 13 is a cutaway view of the electrode array 1200 of FIG. 12 taken along line C:C according to certain aspects of the present disclosure. The substrate 1210 can support the electrodes 1202 on its top surface 1220. Each electrode 1202 can include a base layer 1204 supporting an upper layer 1206 having an upper surface 1208.

FIG. 14 is a cutaway view depicting an electrode array 1400 prior to hydrogel application according to certain aspects of the present disclosure. The electrode array 1400 can be electrode array 1200 of FIG. 12. The electrode array 1400 can include one or more electrodes 1402 supported by a substrate 1410. The electrodes 1402 can include a base layer 1404 and an upper layer 1406. The electrodes 1402 can have a thickness 1412. Any suitable thickness 1412 can be used, such as thickness between about 3 microns to about 6 microns, although other thicknesses can be used, including less than 3 microns and greater than 6 microns. In some cases, the base layer 1404 can have a thickness 1416 that is about three to about five microns in thickness, although other values can be used. In some cases, the upper layer 1406 can have a thickness 1414 that is about 0.5 to about 1 micron in thickness, although other values can be used. In some cases, the base layer 1404 of made of gold or a gold alloy and the upper layer 1406 is made of platinum or a platinum alloy. The electrodes 1402 can have any suitable dimensions, such as about 500 microns to about 2 mm in diameter, although other sizes can be used.

The substrate 1410 can have a thickness 1418 of any suitable size. In some cases, substrate 1410 is thin and flexible to facilitate maneuverability and implantation of the electrode array 1400.

FIG. 15 is a cutaway view depicting an electrode array 1500 with an applied hydrogel layer 1532 according to certain aspects of the present disclosure. The electrode array 1500 can be electrode array 1400 of FIG. 14 after hydrogel 1532 has been applied thereto. The hydrogel 1532 can be applied over the electrodes 1502 and optionally over the substrate 1510.

Figure 16:
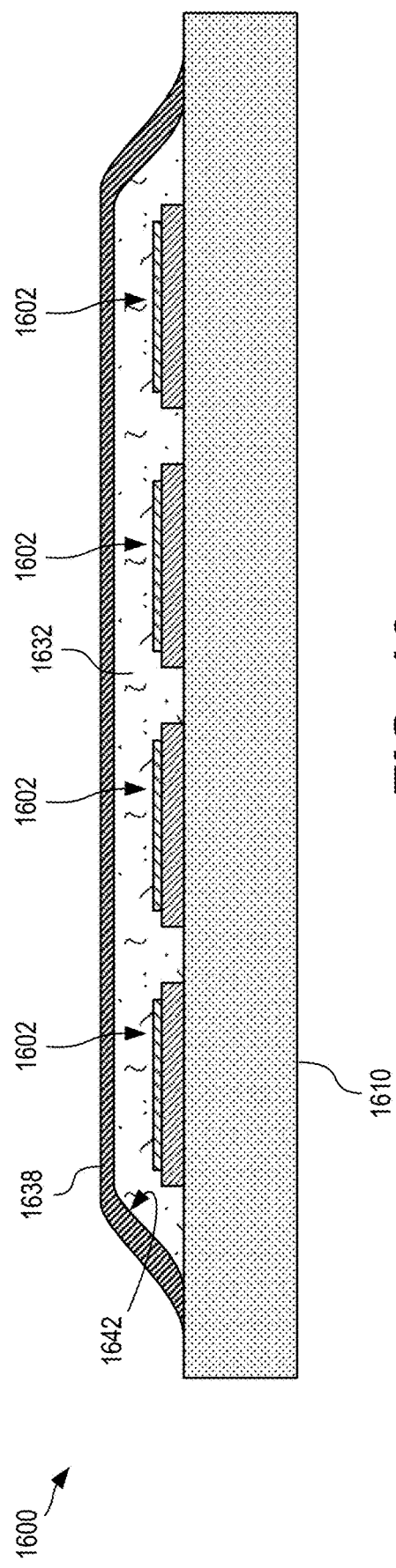
FIG. 16 is a cutaway view depicting an electrode array with a non-swellable shell over an applied hydrogel layer according to certain aspects of the present disclosure.

FIG. 16 is a cutaway view depicting an electrode array 1600 with a non-swellable shell 1638 over an applied hydrogel layer 1632 according to certain aspects of the present disclosure. The electrode array 1600 can be electrode array 1500 of FIG. 15 after a non-swellable shell 1638 has been applied thereto. The non-swellable shell 1638 can be applied over the hydrogel layer 1632 and can couple to the substrate 1610. The non-swellable shell 1638 can couple to the substrate 1610 at locations devoid of hydrogel (e.g., due to masking during hydrogel application). In some cases, a pre-treatment can be applied to the substrate 1610 to facilitate coupling of the non-swellable shell 1638 thereto. The non-swellable shell 1638 can define a cavity 1642 between the non-swellable shell 1638 and the electrodes 1602, which is filled with the hydrogel 1632.

Figure 17:
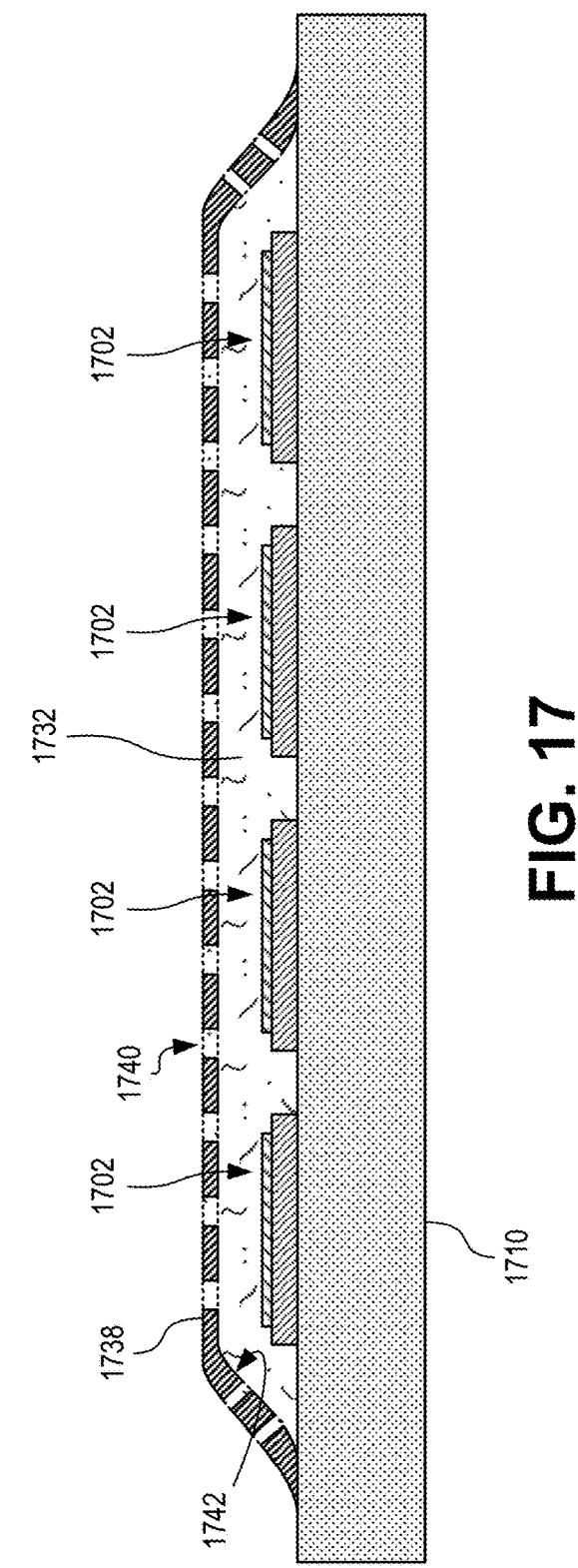
FIG. 17 is a cutaway view depicting an electrode array with a non-swellable shell having openings according to certain aspects of the present disclosure.

FIG. 17 is a cutaway view depicting an electrode array 1700 with a non-swellable shell 1738 having openings 1740 according to certain aspects of the present disclosure. The electrode array 1700 can be electrode array 1600 of FIG. 16 after openings 1740 have been formed in the non-swellable shell 1738. The cavity 1742 defined by the non-swellable shell 1638 and the electrodes 1602 can therefore include openings 1740 through which hydrogel 1632 may pass. Any suitable number and size of openings 1740 can be used. The number and size of openings 1740 can be selected to provide sufficient mechanical retention properties while also providing sufficient electrical conductivity through the non-swellable shell 1738 (e.g., via hydrogel 1732 passing through the openings 1740.

Figure 18:
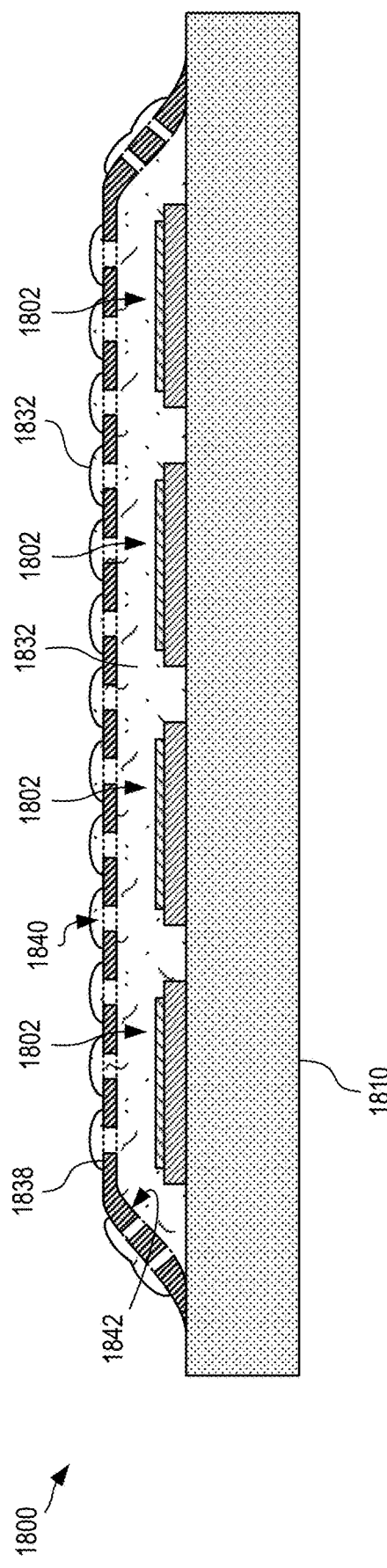
FIG. 18 is a cutaway view depicting an electrode array with hydrogel exposed through openings in a non-swellable shell according to certain aspects of the present disclosure.

FIG. 18 is a cutaway view depicting an electrode array 1800 with hydrogel 1832 exposed through openings 1840 in a non-swellable shell 1838 according to certain aspects of the present disclosure. The electrode array 1800 can be electrode array 1700 of FIG. 17 after sufficient time has passed to allow the hydrogel 1832 to swell through the openings 1840 of the non-swellable shell 1838. The openings 1840 can therefore facilitate electrical conductivity from the outside of the non-swellable shell 1838 to the electrodes 1802 via hydrogel 1832 (e.g., conductive hydrogel) in the cavity 1842 of the non-swellable shell 1838 and swelling out of the openings 1840 of the non-swellable shell 1838.

Figure 19:
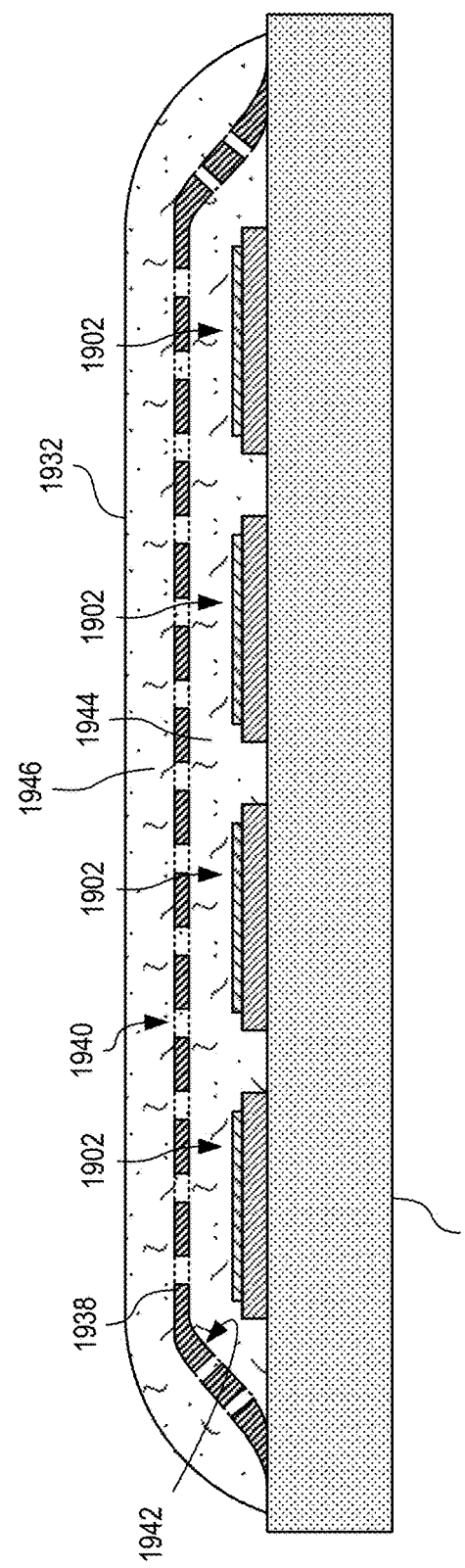
FIG. 19 is a cutaway view depicting an electrode array with an outer hydrogel layer connected to an inner hydrogel layer through openings in a non-swellable shell according to certain aspects of the present disclosure.

FIG. 19 is a cutaway view depicting an electrode array 1900 with an outer hydrogel layer 1946 connected to an inner hydrogel layer 1944 through openings 1940 in a non-swellable shell 1938 according to certain aspects of the present disclosure. The electrode array 1900 can be electrode array 1700 of FIG. 17 after an outer hydrogel layer 1946 has been applied to the outer surface of the non-swellable shell 1938. The outer hydrogel layer 1946 can couple to the inner hydrogel layer 1944 to form a uniform hydrogel mass 1932 that is mechanically held in place by the non-swellable shell 1938 embedded therein. The non-swellable shell 1938 can become embedded within the hydrogel 1932 by coupling of the outer hydrogel layer 1946 to the inner hydrogel layer 1644 through openings 1940. Thus, the openings 1940 can facilitate electrical conductivity from the outside of the non-swellable shell 1938 (e.g., the outer surface of the outer hydrogel layer 1946) to the electrodes 1902 via the hydrogel mass 1932.

FIG. 20 is a cutaway view depicting an electrode array 2000 with hydrogel 2032 anchored using a non-swellable shell 2038 and anchoring features 2022 of the electrodes 2002 that are voids 2034 according to certain aspects of the present disclosure. The electrode array 2000 can be similar to electrode array 1900 of FIG. 19, but with electrodes 2002 having anchoring features 2022 that are voids 2034, similar to electrodes 702 of FIG. 7. Thus, the hydrogel mass 2032 including an outer hydrogel layer 2046 coupled to an inner hydrogel layer 2044 can be secured to the electrodes 2002 via the non-swellable shell 2038 coupled to the substrate 2010 as well as the anchoring features 2022 of the electrodes 2002.

FIG. 21 is a cutaway view depicting an electrode array 2100 with hydrogel 2132 anchored using a non-swellable shell 2138 and anchoring features 2122 of the electrodes 2102 that are apertures 2124 according to certain aspects of the present disclosure. The electrode array 2100 can be similar to electrode array 1900 of FIG. 19, but with electrodes 2102 having anchoring features 2122 that are apertures 2124, similar to electrodes 502 of FIG. 5. Thus, the hydrogel mass 2132 including an outer hydrogel layer 2146 coupled to an inner hydrogel layer 2144 can be secured to the electrodes 2102 via the non-swellable shell 2138 coupled to the substrate 2110 as well as the anchoring features 2122 of the electrodes 2102. In some cases, other anchoring features (e.g., surface textures 936 of FIG. 9) can be used in addition to or instead of anchoring features 2122.

FIG. 22 is a cutaway view depicting an electrode array 2200 with hydrogel 2232 contained within a non-swellable shell 2238 according to certain aspects of the present disclosure. The non-swellable shell 2238 can surround a cross section of the electrode array 2200, thereby forming a cavity 2242 surrounding the electrodes 2202 and substrate 2210 at that particular cross section. Thus, hydrogel 2232 within the cavity 2242 can be located adjacent the electrodes 2202 as well as opposite the substrate 2210 from the electrodes 2202. The non-swellable shell 2238 can include openings 2240 through which hydrogel 2232 can swell out. The electrode array 2200 can be similar to electrode array 1800 of FIG. 18, however with its non-swellable shell 2238 held in place relative to the substrate 2210 via outward pressure from the hydrogel 2232 within the cavity 2242, rather than being directly coupled to the substrate 2210.

FIG. 23 is a cutaway view depicting an electrode array 2300 with an inner hydrogel layer 2344 contained within a non-swellable shell 2338 that is connected to an outer hydrogel layer 2346 through openings 2340 in the non-swellable shell 2338 according to certain aspects of the present disclosure. The non-swellable shell 2338 can surround a cross section of the electrode array 2300, similar to the non-swellable shell 2238 of FIG. 22, thereby forming a cavity 2342 surrounding the electrodes 2302 and substrate 2310 at that particular cross section. Thus, an inner hydrogel layer 2344 within the cavity 2342 can be located adjacent the electrodes 2302 as well as opposite the substrate 2310 from the electrodes 2302. The non-swellable shell 2338 can include openings 2340 through which an outer hydrogel layer 2346 can couple to the inner hydrogel layer 2344 to form a single hydrogel mass 2332. The electrode array 2300 can be similar to electrode array 1900 of FIG. 19, however with its non-swellable shell 2338 held in place relative to the substrate 2310 via outward pressure from the inner hydrogel layer 2344 within the cavity 2342, rather than being directly coupled to the substrate 2310.

As seen in FIG. 23, openings 2340 are depicted in the non-swellable layer 2338 on both the upper side (e.g., nearest the electrodes 2302) and the lower side (e.g., the side opposite the substrate 2310 from the electrodes 2302. In some cases, openings 2340 are only provided in the non-swellable layer 2338 on the side nearest the electrodes 2302. In some cases, openings 2340 are only provided in the non-swellable layer 2338 at locations adjacent the electrodes 2302.

Figure 24:
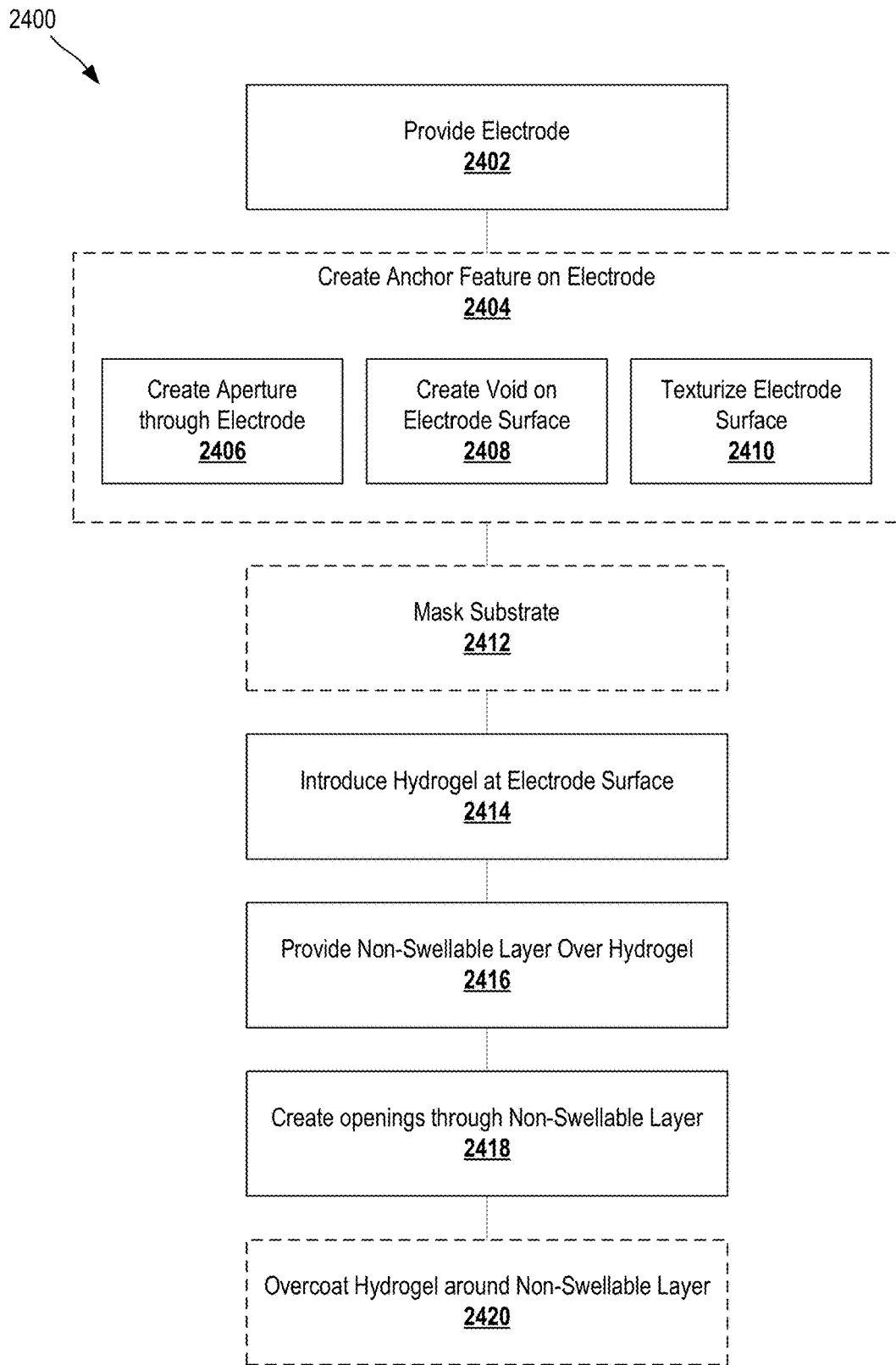
FIG. 24 is a flowchart depicting a process for mechanically securing hydrogel to an electrode using a non-swellable layer according to certain aspects of the present disclosure.

FIG. 24 is a flowchart depicting a process 2400 for mechanically securing hydrogel to an electrode using a non-swellable layer according to certain aspects of the present disclosure. At block 2402, an electrode can be provided. In some cases, the electrode can be pre-manufactured. In some cases, the electrode can be fabricated on a substrate. At optional block 2404, an anchoring feature can be created on the electrode. Any suitable anchoring feature can be created. Creating an anchoring feature can include creating an aperture through the electrode at block 2406, creating a void on the electrode surface at block 2408, or texturizing the electrode surface at block 2410. In some cases, creating an anchor feature at block 2404 can include any combination of block 2406, block 2408, and block 2410. In some cases, other anchoring features can be created at block 2404.

At optional block 2412, the substrate can be masked, such as with a chemical or physical mask. At block 2414, hydrogel can be introduced to the electrode surface. At block 2414, hydrogel may also be introduced to the substrate. In cases where the substrate is masked at block 2412, introducing hydrogel to the substrate at block 2414 can include not introducing or removing hydrogel from the portion of the substrate that was masked at block 2412. In some cases, introducing the hydrogel at block 2414 can first include cleaning the electrodes and/or the substrate.

At block 2416, a non-swellable layer is provided over the hydrogel. In some cases, the non-swellable layer is provided entirely over the hydrogel, such as seen with non-swellable layer 2338 of FIG. 23. In some cases, the non-swellable layer can be coupled to the substrate at block 2416, such as seen in with non-swellable layer 1938 of FIG. 19. In some cases where the non-swellable layer is coupled to the substrate, providing the non-swellable layer at block 2416 can further include first applying a pre-treatment to the substrate and then applying the non-swellable layer to the substrate. In some cases, providing the non-swellable layer at block 2416 can include otherwise coupling the non-swellable layer to the substrate.

In some cases, providing the non-swellable layer at block 2416 can include coupling the non-swellable layer to the substrate at locations between adjacent electrodes, thus reducing electrical conductivity through the inner hydrogel layer between the adjacent electrodes.

In some cases, any sprayable hydrophobic polymer capable of having openings created therein can be used for a non-swellable layer. The term non-swellable layer can include a layer of material exhibiting no or low swelling in vivo.

At block 2418, openings can be created in the non-swellable layer. Openings can be created in any suitable manner, including through photolithography, laser ablation, or other techniques. The openings can pass entirely through the thickness of the non-swellable layer. In some cases, at block 2418 the non-swellable layer can be surface roughened.

At optional block 2420, an additional coating of hydrogel can be applied around the non-swellable layer. This overcoating of hydrogel can result in the hydrogel mass 2332 of FIG. 23.

Figure 25:
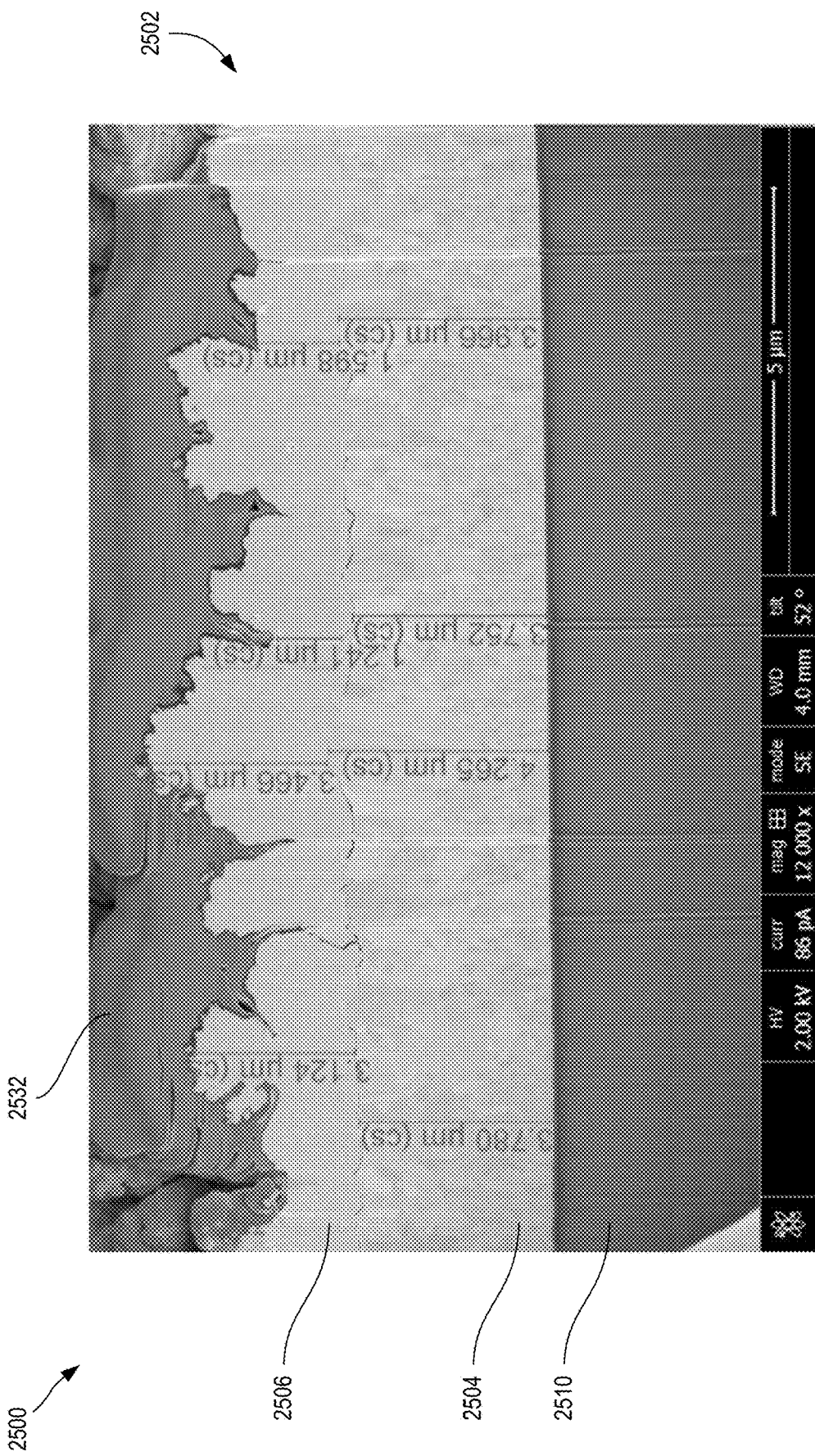
FIG. 25 is a scanning electron micrograph depicting a first example electrode having hydrogel mechanically coupled to a textured anchoring feature according to certain aspects of the present disclosure.

FIG. 25 is a scanning electron micrograph 2500 depicting a first example electrode 2502 having hydrogel 2532 mechanically coupled to a textured anchoring feature according to certain aspects of the present disclosure. The electrode 2502 can be supported by a substrate 2510 and can include a base layer 2504 coupled to an upper layer 2506. The upper layer 2506 can include anchoring features in the form of surface textures, such as surface textures 936 of FIG. 9, into which the hydrogel 2532 can interdigitate. Thus, the hydrogel 2532 can be mechanically affixed to the electrode 2502 without the need to rely substantially on covalent bonds between the hydrogel 2532 and the metal (e.g. noble metal) of the upper layer 2506 of the electrode 2502.

Figure 26:
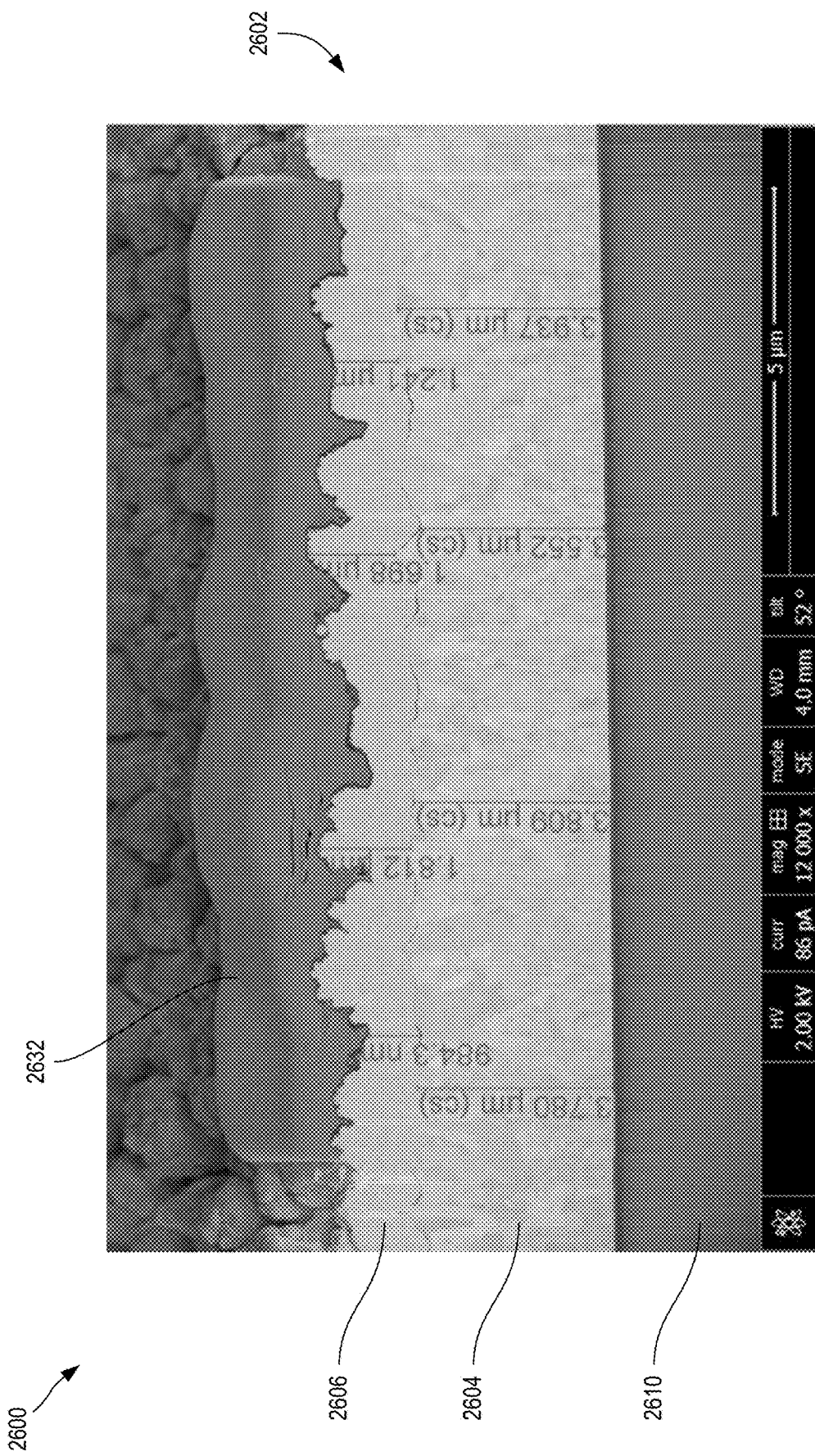
FIG. 26 is a scanning electron micrograph depicting a second example electrode having hydrogel mechanically coupled to a textured anchoring feature according to certain aspects of the present disclosure.

FIG. 26 is a scanning electron micrograph 2600 depicting a second example electrode 2602 having hydrogel 2632 mechanically coupled to a textured anchoring feature according to certain aspects of the present disclosure. The electrode 2602 can be supported by a substrate 2610 and can include a base layer 2604 coupled to an upper layer 2606. The upper layer 2606 can include anchoring features in the form of surface textures, such as surface textures 936 of FIG. 9, into which the hydrogel 2632 can interdigitate. Thus, the hydrogel 2632 can be mechanically affixed to the electrode 2602 without the need to rely substantially on covalent bonds between the hydrogel 2632 and the metal (e.g. noble metal) of the upper layer 2606 of the electrode 2602.

Figure 27:
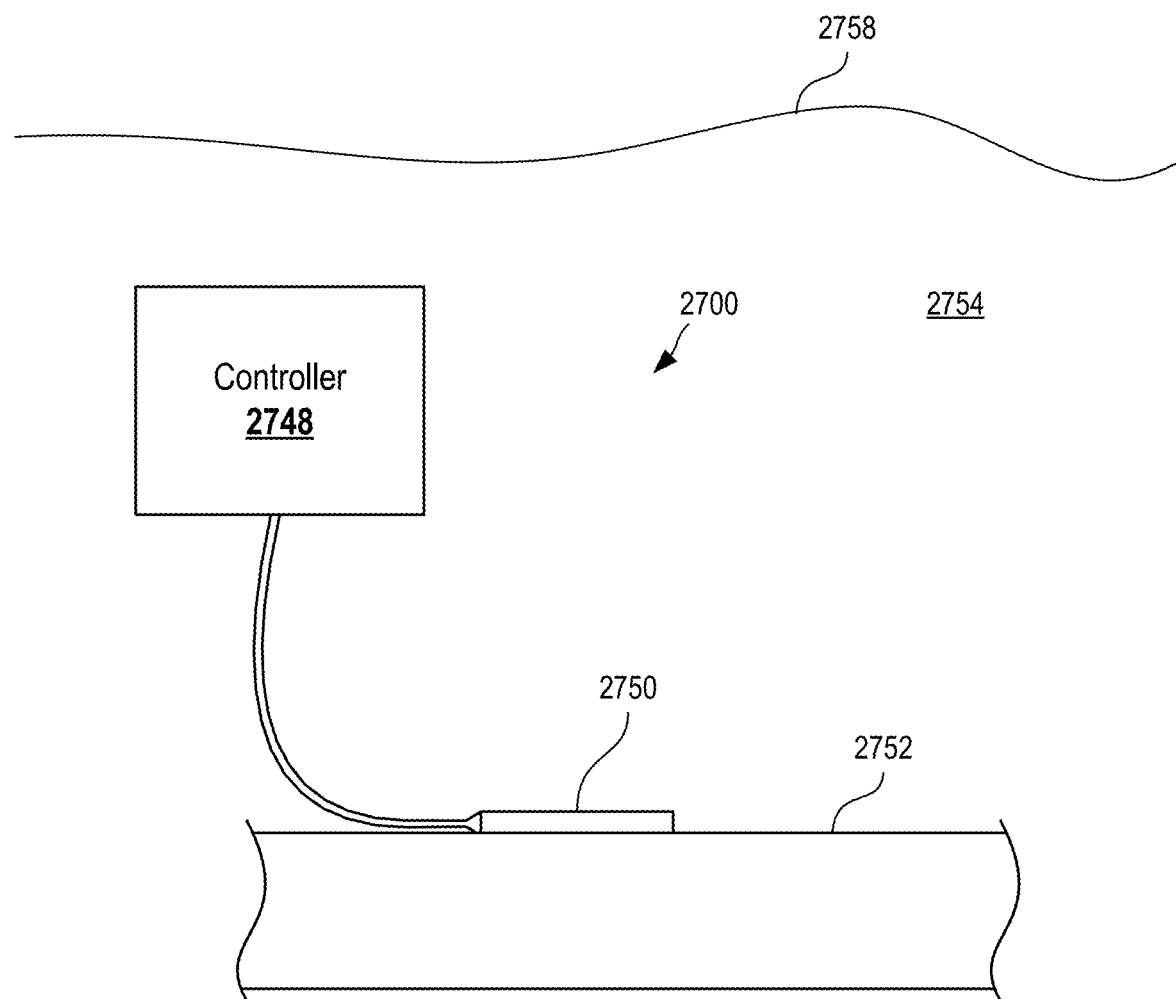
FIG. 27 is a schematic diagram depicting an implantable medical device electrically coupled to biological tissue according to certain aspects of the present disclosure.

FIG. 27 is a schematic diagram depicting an implantable medical device 2700 electrically coupled to biological tissue 2752 according to certain aspects of the present disclosure. The implantable medical device 2700 can include a controller 2748 coupled to an electrode array 2750. The implantable medical device 2700 can be located within a biological cavity 2754 (e.g., within a body of a patient). The implantable medical device 2700 can be separated from an external atmosphere 2756 by skin 2758 or other tissue. The electrode array 2750 can be any electrode array described herein, such as electrode array 2300 of FIG. 23. The electrode array 2750 can be coupled to the biological tissue 2752 using any suitable technique, such as clamps, sutures, pins, screws, adhesives, or other methods. Electrode array 2750 can facilitate electrical communication between the controller 2748 and the biological tissue 2752 by passing electrical signals through the electrodes and hydrogel of the electrode array 2750. Thus, electrode array 2750 can operate to send, receive, or send and receive electrical signals to, from, or to and from biological tissue 2752. Thus, electrode array 2750 can be suitable for use as a stimulation device, a measurement device, or any combination thereof.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is an implantable electrode array, comprising: at least one electrode comprising a conductible metal layer having one or more anchoring features; and a hydrogel layer mechanically coupled to the conductible metal layer at the one or more anchoring features.

Example 2 is the electrode array of example 1, wherein the one or more anchoring features include an aperture passing through a thickness of the at least one electrode.

Example 3 is the electrode array of examples 1 or 2, wherein the one or more anchoring features include a void having a depth that is less than a thickness of the at least one electrode.

Example 4 is the electrode array of examples 1-3, further comprising a substrate having at least one additional anchoring feature, wherein the at least one electrode is coupled to the substrate, and wherein the hydrogel layer is further mechanically coupled at the at least one additional anchoring feature.

Example 5 is the electrode array of examples 1-4, wherein the hydrogel layer comprises electrically conductive hydrogel material.

Example 6 is the electrode array of examples 1-5, wherein the hydrogel layer comprises a non-swelling hydrogel material or a low-swell hydrogel material.

Example 7 is the electrode array of examples 1-6, wherein the conductible metal layer is a noble metal.

Example 8 is the electrode array of example 7, wherein the conductible metal layer is selected from the group consisting of platinum and gold.

Example 9 is an implantable device, comprising: an electrode array positionable adjacent biological tissue, the electrode array comprising: at least one electrode comprising a conductible metal layer having one or more anchoring features; and a hydrogel layer mechanically coupled to the conductible metal layer at the one or more anchoring features, wherein the hydrogel layer is located between the at least one electrode and the biological tissue for conducting a signal between the at least one electrode and the biological tissue when the electrode array is positioned adjacent the biological tissue; and a controller electrically coupled to the electrode array.

Example 10 is the implantable device of example 9, wherein the one or more anchoring features include an aperture passing through a thickness of the at least one electrode.

Example 11 is the electrode array of examples 9 or 10, wherein the one or more anchoring features include a void having a depth that is less than a thickness of the at least one electrode.

Example 12 is the electrode array of examples 9-11, further comprising a substrate having at least one additional anchoring feature, wherein the at least one electrode is coupled to the substrate, and wherein the hydrogel layer is further mechanically coupled at the at least one additional anchoring feature.

Example 13 is the electrode array of examples 9-12, wherein the hydrogel layer comprises electrically conductive hydrogel material.

Example 14 is the electrode array of examples 9-13, wherein the hydrogel layer comprises a non-swelling hydrogel material or a low-swell hydrogel material.

Example 15 is the electrode array of examples 9-14, wherein the conductible metal layer is a noble metal.

Example 16 is the electrode array of example 15, wherein the conductible metal layer is selected from the group consisting of platinum and gold.

Example 17 is a method of preparing an electrode array, comprising: providing an electrode comprising a conductible metal layer; creating one or more anchoring features on the conductible metal layer; and introducing a hydrogel layer, wherein introducing the hydrogel layer includes mechanically securing the hydrogel layer against the conductible metal layer using the one or more anchoring features.

Example 18 is the method of example 17, wherein creating the one or more anchoring features includes creating at least one aperture through a thickness of the at least one electrode.

Example 19 is the method of examples 17 or 18, wherein creating the one or more anchoring features includes creating a void in the conductible metal layer extending from a surface of the conductible metal layer to a depth that is less than a thickness of the at least one electrode.

Example 20 is the method of examples 17-19, wherein providing the electrode includes applying the conductible metal layer to a substrate, the method further comprising creating at least one additional anchoring feature in the substrate, wherein introducing the hydrogel layer further includes mechanically securing the hydrogel layer using the at least one additional anchoring feature.

Example 21 is the method of examples 17-20, wherein the hydrogel layer comprises electrically conductive hydrogel material.

Example 22 is the method of examples 17-21, wherein the hydrogel layer comprises a non-swelling hydrogel material or a low-swell hydrogel material.

Example 23 is the method of examples 17-22, wherein the conductible metal layer is a noble metal.

Example 24 is the method of example 23, wherein the conductible metal layer is selected from the group consisting of platinum and gold.

Example 25 is an electrode array, comprising: at least one electrode comprising a conductible metal layer; a substrate supporting the at least one electrode; a non-swellable material defining an internal cavity surrounding the at least one electrode, the non-swellable material having one or more openings; and hydrogel material disposed within the internal cavity between the non-swellable material and the at least one electrode, wherein the non-swellable material mechanically secures the hydrogel material against the at least one electrode.

Example 26 is the electrode array of example 25, further comprising additional hydrogel material disposed opposite the non-swellable material from the internal cavity, wherein the additional hydrogel material contacts the hydrogel material.

Example 27 is the electrode array of examples 25 or 26, wherein the non-swellable material is coupled to the top surface of the substrate, and wherein the internal cavity is defined in part by at least a portion of the top surface of the substrate.

Example 28 is the electrode array of examples 25-27, wherein the internal cavity is sized to surround at least a portion of a bottom surface of the substrate, and wherein the hydrogel material is further disposed within the internal cavity between the non-swellable material and the bottom surface of the substrate.

Example 29 is the electrode array of examples 25-28, wherein the conductible metal layer of the at least one electrode includes one or more anchoring features, and wherein the hydrogel material is further mechanically coupled to the at least one electrode at the one or more anchoring features.

Example 30 is the electrode array of examples 25-29, wherein the substrate includes at least one additional anchoring feature, and wherein the hydrogel layer is further mechanically coupled at the at least one additional anchoring feature.

Example 31 is the electrode array of examples 25-30, wherein the hydrogel layer comprises electrically conductive hydrogel material.

Example 32 is the electrode array of examples 25-31, wherein the hydrogel layer comprises a non-swelling hydrogel material or a low-swell hydrogel material.

Example 33 is the electrode array of examples 25-32, wherein the conductible metal layer is a noble metal.

Example 34 is the electrode array of example 33, wherein the conductible metal layer is selected from the group consisting of platinum and gold.

Example 35 is an implantable device, comprising: an electrode array positionable adjacent biological tissue, the electrode array comprising: at least one electrode comprising a conductible metal layer; a substrate supporting the at least one electrode; a non-swellable material defining an internal cavity surrounding the at least one electrode, the non-swellable material having one or more openings; and hydrogel material disposed within the internal cavity between the non-swellable material and the at least one electrode, wherein the non-swellable material mechanically secures the hydrogel material against the at least one electrode, and wherein at least a portion of the hydrogel extends through the one or more openings for electrically coupling to the biological tissue and conducting a signal between the at least one electrode and the biological tissue when the electrode array is positioned adjacent the biological tissue; and a controller electrically coupled to the electrode array.

Example 36 is the implantable device of example 35, wherein the electrode array further comprises additional hydrogel material disposed opposite the non-swellable material from the internal cavity, wherein the additional hydrogel material contacts the hydrogel material for electrically coupling the hydrogel material to the biological tissue through the additional hydrogel material.

Example 37 is the implantable device of examples 35 or 36, wherein the non-swellable material is coupled to the top surface of the substrate, and wherein the internal cavity is defined in part by at least a portion of the top surface of the substrate.

Example 38 is the implantable device of examples 35-37, wherein the internal cavity is sized to surround at least a portion of a bottom surface of the substrate, and wherein the hydrogel material is further disposed within the internal cavity between the non-swellable material and the bottom surface of the substrate.

Example 39 is the implantable device of examples 35-38, wherein the conductible metal layer of the at least one electrode includes one or more anchoring features, and wherein the hydrogel material is further mechanically coupled to the at least one electrode at the one or more anchoring features.

Example 40 is the implantable device of examples 35-39, wherein the substrate includes at least one additional anchoring feature, and wherein the hydrogel layer is further mechanically coupled at the at least one additional anchoring feature.

Example 41 is the implantable device of examples 35-40, wherein the hydrogel layer comprises electrically conductive hydrogel material.

Example 42 is the implantable device of examples 35-41, wherein the hydrogel layer comprises a non-swelling hydrogel material or a low-swell hydrogel material.

Example 43 is the implantable device of examples 35-42, wherein the conductible metal layer is a noble metal.

Example 44 is the implantable device of example 43, wherein the conductible metal layer is selected from the group consisting of platinum and gold.

Example 45 is a method of preparing an electrode array, comprising: providing an electrode on a substrate, the electrode comprising a conductible metal layer; applying hydrogel material to the electrode; coating the hydrogel material with a non-swellable material, wherein the non-swellable material mechanically secures the hydrogel layer to the electrode; and creating one or more openings in the non-swellable material to expose the hydrogel material.

Example 46 is the method of example 45, wherein coating the hydrogel material with the non-swellable material includes coupling the non-swellable material to the substrate.

Example 47 is the method of examples 45 or 46, further comprising masking a first portion of the substrate prior to applying the hydrogel material to the electrode, wherein coating the hydrogel material with the non-swellable material includes coupling the non-swellable material to the first portion of the substrate.

Example 48 is the method of examples 45-47, further comprising overcoating the non-swellable material with additional hydrogel material, wherein the additional hydrogel contacts the hydrogel material through the openings in the non-swellable material.

Example 49 is the method of examples 45-48, further comprising creating one or more anchoring features on the conductible metal layer, wherein applying hydrogel material to the electrode includes mechanically securing the hydrogel layer against the conductible metal layer using the one or more anchoring features.

Example 50 is the method of examples 45-49, wherein the hydrogel layer comprises electrically conductive hydrogel material.

Example 51 is the method of examples 45-50, wherein the hydrogel layer comprises a non-swelling hydrogel material or a low-swell hydrogel material.

Example 52 is the method of examples 45-51, wherein the conductible metal layer is a noble metal.

Example 53 is the method of example 52, wherein the conductible metal layer is selected from the group consisting of platinum and gold.

What is claimed is:

1. An electrode array, comprising:
    at least one electrode comprising a conductible metal layer;
    a substrate supporting the at least one electrode;
    hydrogel material disposed over the at least one electrode; and
    a non-swellable coating surrounding the at least one electrode and disposed over the hydrogel material, wherein the non-swellable coating:
        includes one or more ends that are chemically anchored to a surface of the substrate;
        conforms to a shape of the hydrogel material; and
        mechanically secures the hydrogel material against the at least one electrode.

2. The electrode array of claim 1, further comprising additional hydrogel material disposed over the non-swellable coating, wherein:

the additional hydrogel material contacts the hydrogel material through one or more openings of the non-swellable coating; and
the hydrogel material and the additional hydrogel material secure a position of the non-swellable coating.

3. The electrode array of claim 1, wherein the non-swellable coating includes an internal cavity that is defined in part by at least a portion of a surface of the substrate.

4. The electrode array of claim 1, wherein the one or more ends of the non-swellable coating are anchored to a location of the surface that is devoid of the hydrogel material.

5. The electrode array of claim 1, wherein the conductible metal layer of the at least one electrode includes one or more anchoring features, and wherein the hydrogel material is further mechanically coupled to the at least one electrode at the one or more anchoring features.

6. The electrode array of claim 1, wherein the substrate includes at least one anchoring feature, and wherein the hydrogel material is mechanically coupled at the at least one anchoring feature.

7. The electrode array of claim 1, wherein the hydrogel material is electrically conductive.

8. The electrode array of claim 1, wherein the hydrogel material is a non-swelling hydrogel material or a low-swell hydrogel material.

9. The electrode array of claim 1, wherein the conductible metal layer is a noble metal.

10. The electrode array of claim 9, wherein the conductible metal layer is selected from the group consisting of platinum and gold.

11. An implantable device, comprising:
an electrode array comprising:
at least one electrode comprising a conductible metal layer;
a substrate supporting the at least one electrode;
hydrogel material disposed over the at least one electrode; and
a non-swellable coating surrounding the at least one electrode and disposed over the hydrogel material, wherein the non-swellable coating:
includes one or more ends that are chemically anchored to a surface of the substrate;
conforms to a shape of the hydrogel material;
mechanically secures the hydrogel material against the at least one electrode; and
includes one or more openings, wherein at least a portion of the hydrogel material extends swells through the one or more openings to conduct an electric signal between the at least one electrode and a biological tissue when the electrode array is positioned adjacent the biological tissue; and
a controller electrically coupled to the electrode array.

12. The implantable device of claim 11, wherein the electrode array further comprises additional hydrogel material disposed over the non-swellable coating, wherein:
the additional hydrogel material contacts the hydrogel material through the one or more openings of the non-swellable coating to conduct the electric signal from the hydrogel material through the additional hydrogel material; and
the hydrogel material and the additional hydrogel material secure a position of the non-swellable coating.

13. The implantable device of claim 11, wherein the non-swellable coating includes an internal cavity that is defined in part by at least a portion of a surface of the substrate.

14. The implantable device of claim 11, wherein the one or more ends of the non-swellable coating are anchored to a location of the surface that is devoid of the hydrogel material.

15. The implantable device of claim 11, wherein the conductible metal layer of the at least one electrode includes one or more anchoring features, and wherein the hydrogel material is further mechanically coupled to the at least one electrode at the one or more anchoring features.

16. The implantable device of claim 11, wherein the substrate includes at least one anchoring feature, and wherein the hydrogel material is mechanically coupled at the at least one anchoring feature.

17. The implantable device of claim 11, wherein the hydrogel material is electrically conductive.

18. The implantable device of claim 11, wherein the hydrogel material is a non-swelling hydrogel material or a low-swell hydrogel material.

19. The implantable device of claim 11, wherein the conductible metal layer is a noble metal.

20. The implantable device of claim 19, wherein the conductible metal layer is selected from the group consisting of platinum and gold.

21. A method of preparing an electrode array, comprising:
providing an electrode on a substrate, the electrode comprising a conductible metal layer;
applying hydrogel material over the electrode;
coating the hydrogel material with a non-swellable coating, wherein the non-swellable coating:
includes one or more ends that are chemically anchored to a surface of the substrate;
conforms to a shape of the hydrogel material; and
mechanically secures the hydrogel material to the electrode; and
creating one or more openings in the non-swellable coating to expose the hydrogel material to a biological tissue.

22. The method of claim 21, wherein coating the hydrogel material with the non-swellable coating includes coupling the one or more ends of the non-swellable coating to surface of the substrate.

23. The method of claim 21, further comprising masking a first portion of the substrate prior to applying the hydrogel material over the electrode, wherein coating the hydrogel material with the non-swellable coating includes coupling the one or more ends to the first portion of the substrate.

24. The method of claim 21, further comprising overcoating the non-swellable coating with additional hydrogel material, wherein the additional hydrogel material contacts the hydrogel material through the one or more openings in the non-swellable coating.

25. The method of claim 21, further comprising creating one or more anchoring features on the conductible metal layer, wherein applying hydrogel material to the electrode includes mechanically securing the hydrogel material against the conductible metal layer using the one or more anchoring features.

26. The method of claim 21, wherein the hydrogel material comprises electrically conductive hydrogel material.

27. The method of claim 21, wherein the hydrogel material comprises a non-swelling hydrogel material or a low-swell hydrogel material.

28. The method of claim 21, wherein the conductible metal layer is a noble metal.

29. The method of claim 28, wherein the conductible metal layer is selected from the group consisting of platinum and gold.

* * * * *